United States Patent
Comb et al.

(10) Patent No.: US 11,352,418 B2
(45) Date of Patent: Jun. 7, 2022

(54) ANALYSIS OF UBIQUITINATED POLYPEPTIDES

(71) Applicant: Cell Signaling Technology, Inc., Danvers, MA (US)

(72) Inventors: Michael J. Comb, Manchester, MA (US); John Edward Rush, II, Beverly, MA (US); Jing Li, Brighton, MA (US); Ailan Guo, Lexington, MA (US)

(73) Assignee: CELL SIGNALING TECHNOLOGY, INC., Danvers, MA (US)

( * ) Notice: Subject to any disclaimer, the term of this patent is extended or adjusted under 35 U.S.C. 154(b) by 0 days.

(21) Appl. No.: 16/508,991

(22) Filed: Jul. 11, 2019

(65) Prior Publication Data
US 2020/0131254 A1    Apr. 30, 2020

Related U.S. Application Data

(60) Continuation of application No. 14/572,194, filed on Dec. 16, 2014, now abandoned, which is a continuation-in-part of application No. 13/856,933, filed on Apr. 4, 2013, now Pat. No. 9,181,326, which is a division of application No. 12/967,284, filed on Dec. 14, 2010, now abandoned, said application No. 14/572,194 is a continuation-in-part of application No. 11/484,485, filed on Jul. 11, 2006, now Pat. No. 9,085,609.

(60) Provisional application No. 61/286,486, filed on Dec. 15, 2009.

(51) Int. Cl.
*C07K 16/18*    (2006.01)

(52) U.S. Cl.
CPC ......... *C07K 16/18* (2013.01); *C07K 2317/24* (2013.01); *C07K 2317/34* (2013.01); *C07K 2317/92* (2013.01)

(58) Field of Classification Search
CPC ............................................. C07K 16/00–468
See application file for complete search history.

(56) References Cited

U.S. PATENT DOCUMENTS

| | | | |
|---|---|---|---|
| 5,532,167 A | 7/1996 | Cantley et al. |
| 5,538,897 A | 7/1996 | Yates, III et al. |
| 5,593,844 A | 1/1997 | Carlsson et al. |
| 5,679,769 A | 10/1997 | Danishefsky et al. |
| 5,716,836 A | 2/1998 | Suiko |
| 5,759,787 A | 6/1998 | Strulovici |
| 5,885,841 A | 3/1999 | Higgs, Jr. et al. |
| 5,932,102 A | 8/1999 | Wyllie et al. |
| 5,965,352 A | 10/1999 | Stoughton et al. |
| 6,001,580 A | 12/1999 | Tani et al. |
| 6,017,693 A | 1/2000 | Yates, III et al. |
| 6,291,645 B1 | 9/2001 | Shin et al. |
| 6,322,970 B1 | 11/2001 | Little et al. |
| 6,379,970 B1 | 4/2002 | Liebler et al. |
| 6,441,140 B1 | 8/2002 | Comb et al. |
| 6,451,591 B1 | 9/2002 | Edwards |
| 6,489,136 B1 | 12/2002 | Zervos |
| 6,576,469 B1 | 6/2003 | Struhl et al. |
| 6,579,720 B1 | 6/2003 | Pidgeon et al. |
| 6,818,454 B2 | 11/2004 | Goshe et al. |
| 6,982,318 B1 | 1/2006 | Comb et al. |
| 7,198,896 B2 | 4/2007 | Rush et al. |
| 7,259,022 B2 | 8/2007 | Comb et al. |
| 7,300,753 B2 | 11/2007 | Rush et al. |
| 7,344,714 B2 | 3/2008 | Comb et al. |
| 9,085,609 B2 | 7/2015 | Comb et al. |
| 9,181,326 B2 | 11/2015 | Rush, II et al. |
| 2002/0168684 A1 | 11/2002 | Comb et al. |
| 2006/0148093 A1 | 7/2006 | Gygi et al. |
| 2008/0008699 A1 | 1/2008 | Li et al. |
| 2009/0022659 A1 | 1/2009 | Olson et al. |
| 2009/0317409 A1 | 12/2009 | Xu et al. |
| 2012/0149883 A1 | 6/2012 | Gygi et al. |
| 2014/0094594 A1 | 4/2014 | Rush et al. |
| 2015/0259405 A1 | 9/2015 | Comb et al. |

FOREIGN PATENT DOCUMENTS

| | | |
|---|---|---|
| EP | 0054492 | 6/1982 |
| WO | 98/29452 | 7/1998 |
| WO | 9919597 A1 | 4/1999 |
| WO | 0014536 A1 | 3/2000 |
| WO | 0127624 A2 | 4/2001 |

(Continued)

OTHER PUBLICATIONS

Kemp et al. "Protein kinase recognition sequence motifs," Trends Biochem. Sci., vol. 15, No. 9, pp. 342-346 (1990).
Keranen et al. "Protein Kinase C is Regulated In Vivo by Three Functionally Distinct Phosphorylations," Curr. Biol., vol. 5, pp. 1394-1403 (1995).
Kushima et al. "Characterization of HPC-1 antigen, an isoform of syntaxin-1, with the isoform-specific monoclonal antibody, 14D8," J. Mol. Neurosci., vol. 8, No. 1, pp. 19-26 (1997).
Miceli et al. "Two-stage selection of sequences from a random phage display library delineates both core residues and permitted structural range within an epitope," J. Immun Methods, vol. 167, Nos. 1-2, 3, pp. 279-287 (1994).
Montminy "Transcriptional Regulation by Cyclic AMP," Annu. Rev. Biochem., vol. 66, pp. 807-822 (1997).

(Continued)

*Primary Examiner* — Jessica H Roark
(74) *Attorney, Agent, or Firm* — DLA Piper LLP US

(57) ABSTRACT

The disclosure relates to antibody reagents that specifically bind to peptides carrying a ubiquitin remnant from a digested or chemically treated biological sample. The reagents allow the technician to identify ubiquitinated polypeptides as well as the sites of ubiquitination on them. The reagents are preferably employed in proteomic analysis using mass spectrometry. The antibody reagents specifically bind to the remnant of ubiquitin (i.e., a diglycine modified epsilon amine of lysine) left on a peptide which as been generated by digesting or chemically treating ubiquitinated proteins. The inventive antibody reagents' affinity to the ubiquitin remnant does not depend on the remaining amino acid sequences flanking the modified (i.e., ubiquitinated) lysine, i.e., they are context independent.

8 Claims, 2 Drawing Sheets

Specification includes a Sequence Listing.

(56) References Cited

FOREIGN PATENT DOCUMENTS

| WO | 2005083113 A1 | 9/2005 |
|---|---|---|
| WO | 2005083439 A1 | 9/2005 |
| WO | 2005083444 A1 | 9/2005 |

OTHER PUBLICATIONS

Muslin et al. Cell, "Interaction of 14-3-3 with signaling proteins is mediated by the recognition of phosphoserine", vol. 84, pp. 889-897 (1996).
Levine et al. "Antibodies and radioimmunoassays for phosphoserine, phosphothreonine and phosphotyrosine Serologic specificities and levels of the phosphoamino acids in cytoplasmic fractions of rat tissues," Journal of Immunological Methods, vol. 124, No. 2, pp. 239-249 (1989).
Lichtenberg-Kraag et al. "Phosphorylation-dependent eptiopes of neurofilament antibodies on tau protein and relationship with Alzheimber tau," Proc. Natl. Acad. Sci. USA, vol. 89, pp. 5384-5388 (Jun. 1992).
Nishilawa et al. "Determination ofthe Specific Substrate Sequence Motifs of Protein Kinase C Isozymes," J. Biol. Chem., vol. 272, No. 2, pp. 952-960 (1990).
Pap et al. "Role of Glycogen Synthase Kinase-3 in the Phosphatidylinositol3-Kinase/Akt Cell Survival Pathway," J. Biol. Chem., vol. 273, No. 32, pp. 19929-19932 (1998).
Peng et al. Science, "Mitotic and G2 checkpoint control: regulation of 14-3-3 protein binding by phosphorylation of Cdc25C on serine-216", vol. 277, pp. 1501-1508 (1997).
Pinilla et al. "Elucidation of monoclonal antibody polyspecificity using a synthetic combinatorial library", Peptide Research, vol. 8, pp. 250-257 (1995).
Poulter et al. "Locations and Immunoreactivities of Phosphorylation Sites on Bovine and Porcine Tau Proteins and a PHF-Tau Fragment," J Biol Chem., vol. 268., No. 13, pp. 9636-9644 (1993).
Reichmann et al. "Reshaping human antibodies for therapy," Nature, vol. 332, pp. 323-327 (1988).
Rosenberg et al. "Characterization of a Distinct Binding Site for the Prokaryotic Chaperone, GroEL, on a Human Granulocyte Ribonuclease," J. Biol. Chem., vol. 268, No. 6, pp. 4499-4503 (1993).
Ross et al. "Phosphotyrosine-containing proteins isolated by affinity chromatography with antibodies to synthetic hapten," Nature, vol. 294, pp. 654-656 (1981).
Songyang et al. "Use of an oriented peptide library to determine the optimal substrates of protein kinases," Curr. Bio., vol. 4, No. 11, pp. 973-982 (1994).
Songyang et al. "A structural basis for substrate specificities of protein Ser/Thr-kinases: Primary sequence preference of casein kinase I and II, NIMA, phosphorylase kinase, CaM kinase II, CDK5 and Erkl," Mol. Cell. Biol., vol. 16, pp. 6486-6493 (1996).
Struhl "Histone acetylation and transcriptional regulatory mechanisms," Genes & Dev., vol. 12, pp. 599-606 (1998).
Stukenberg et al. "Systematic identification of mitotic phosphoproteins," Current Biology, vol. 7, No. 5, pp. 338-348 (1997).
Suzuki et al. "Antibody specific for the Thr-286-autophosphorylated a subunit of Ca2+ /calmodulin-dependent protein kinase II," Proc. Natl. Acad. Sci. USA, vol. 89, pp. 109-113 (1992).
Verhoeven et al. "Reshaping human antibodies: Grafting an antilysozyme activity," Science, vol. 239, pp. 1534-1536 (1988).
Westendorf "Cloning of cDNAs for M-phase phosphoproteins recognized by the MPM2 monoclonal antibody and determination of the phosphorylated epitope," Proc. Natl. Acad. Sci. USA, vol. 91, pp. 714-718 (1994).
Yaffe et al. "The Structural Basis for 14-3-3: Phosphopeptide Binding Specificity," Cell, vol. 91, pp. 961-971 (1997).
Yaffe et al. "Sequence-specific and phosphorylationdependent proline isomerization: a potential mitotic regulatory mechanism," Science, vol. 278, No. 5345, pp. 1957-1960 (1997).
Yaffe et al. "A motif-based profile scanning approach for genome-wide prediction of signaling pathways," Nature Biotech., vol. 19, pp. 348-353 (2001).
Zha et al. "Serine Phosphorylation of Death Agonist BAD in Response to Survival Factor Results in Binding to 14-3-3 Not BCL-X," Cell, vol. 87, No. 4, pp. 619-628 (1996).
Current Protocols in Immunology, Unit 9.3: Selection of Immunogenic Peptides for Antisera Production 9.31-9.3.3 (1991).
Protein Phosphorylation: A Practical Approach, ed. Hardie, p. 267, IRL Press (1993).
Sigma 1998 Catalog, pp. 1305 and 1309.
Upstate Biotechnology 1998 Catalog, p. 17.
Zymed Laboratories 1996-1997 General Catalog, p. 80.
United States Patent and Trademark Office, Office Action dated Dec. 4, 2012 pertaining to U.S. Appl. No. 12/967,284, 43 pages.
Cell Signaling Technology Inc.'s 2000-2001 Catalogue, pp. 14 and 198.
Rudikoff et al., "Single amino acid substitution altering antigen-binding specificity", Proc Natl Acad Sci USA 1982 vol. 79 p. 1979-1983.
Yamaguchi et al., "Substrate specificity of the human protein phosphatase 2Cdelta, Wip1", Biochem 2005; 44:5285-94.
Zhao et al., "The mechanism of dephosphorylation of extracellular signal-regulated kinase 2 by mitogen-activated protein kinase phosphatase 3", J Biol. Chem. 2001; 276:32382-91.
Katou et al., "Catalytic activation of the plant MAPK phosphatase NtMKP1 by its physiological substrate salicylic acid-induced protein kinase but not by calmodulins", J. Biol. Chem., 2005; 280:39569-81.
Martinez-Martinez et al., "Blockade of NFAT activation by the second calcineurin binding site", J. Biol. Chem., Mar. 10, 2006; 281:6227-6235.
Donella-Deana et al., "Dephosphorylation of phosphopeptides by calcineurin (protein phosphatase 2B)", Eur. J. Biochem 1994; 219:109-17.
Boisvert et al., "A proteomic analysis of arginine-methylated protein complexes", Mol Cell Proteomics 2003; 2:1319-30.
Brahms et al., "The C-terminal RG dipeptide repeats of the spliceosomal Sm proteins D1 and D3 contain symmetrical dimethylarginines, which form a major B-cell epitope for anti-Sm autoantibodies", J. Biol. Chem. 2000; 275:17122-29.
Siebel et al., "The essential yeast RNA binding protein Np13p is methylated", Proc Nat'l Acad Sci. 1996; 93:13641-46.
AB412 Datasheet (Abcam monoclonal antibody 7E6), downloaded from Abcam website Sep. 18, 2013.
Hebbes et al., Mol. Immunol., "A "minimal epitope" anti-protein antibody that recognises a single modified amino acid", 1989; 26:865-73.
Komatsu et al., "Four different clones of mouse anti-acetyllysine monoclonal antibodies having different recognition properties share a common immunoglobulin framework structure", J Immunol Meth 2003; 272:161-75.
Hinson et al. "Immunochemical detection of drug-protein adducts in acetaminophen hepatotoxicity", Adv Exp Med Biol, 1996, vol. 387, pp. 47-55.
Pearson and Kemp "Protein kinase phosphorylation site sequences and consensus specificity motifs: tabulations", Methods in Enzymology, 1991, vol. 200, pp. 62-81.
Knappik et al., "Fully synthetic human combinatorial antibody libraries (HuCAL) based on modular consensus frameworks and CDRs randomized with trinucleotides", Journal of Molecular Biology, 296(11):57-86 (2000).
Tanaka et al., "The Ligation Systems for Ubiquitin and Ubiquitin-like Proteins", Molecules and Cells, 8(5):503-512 (1998).
Peng et al., "A proteomics approach to understanding protein ubiquitination", Nature Biotechnology, 21(8):921-926 (2003).
Denis et al., "Tryptic digestion of ubiquitin standards reveals an improved strategy for identifying ubiquitinated proteins by mass spectrometry", Proteomics, 7:868-874 (2007).
Al-Obeidi et al. "Protein tyrosine kinases: Structure, substrate specificity, and drug discovery," Biopolymers, vol. 47, pp. 197-223 (1998).

(56) References Cited

OTHER PUBLICATIONS

Alessi et al. "Mechanism of activation of protein kinase B by insulin and IGF-1," The EMBO J., vol. 15, No. 23, pp. 6541-6551 (1996).
Alessi et al. "Molecular basis for the substrate specificity of protein kinase B; comparison with MAPKAP kinase-1 and p70 S6 kinase," FEBS Lett., vol. 399, No. 3, pp. 333-338 (1996).
Bangalore et al. "Antiserum raised against a synthetic phosphotyrosine-containing peptide selectively recognized p185neu/erbB-Z and the epidermal growth factor receptor," Proc. Nat/. Acad. Sci. USA, vol. 89, pp. 11637-11641 (1992).
Blaukat et al. "Determination of Bradykinin B2 Receptor in Vivo Phosphorylation Sites and Their Role in Receptor Function," J. Bioi. Chem., vol. 276, No. 44, pp. 40431-40440 (2001).
Brunet et al. "Akt Promotes Cell Survival by Phosphorylating and Inhibiting a Forkhead Transcription Factor," Cell, vol. 96, pp. 857-868 (1999).
Burbelo et al. "14-3-3 Proteins: Hot numbers in signal transduction," Curr. Bioi., vol. 5, No. 2, pp. 95-96 (1995).
Capra et al. "The Antibody Combining Site" Sci. Am., vol. 236, pp. 50-59 (1977).
Cardone et al. "Regulation of Cell Death Protease Caspase-9 by Phosphorylation," Science, vol. 282, No. 5392, pp. 1318-1321 (1998).
Cantley Cell Signaling Technology Inc.'s 2000-2001 Catalogue, p. 198.
Czernik et al. "Production of phosphorylation state-specific antibodies." Methods Enzymol., vol. 201, pp. 264-283 (1991).
Czernik et al. "Phosphorylation State-Specific antibodies: Preparation and Applications." Neuroprotocols., vol. 6, pp. 56-61 (1995).
Dalby et al. Identification of Regulatory Phosphoylation Sites in Mitogen-activated Protein Kinase (MAPK)-activated Protein Kinase-1 a/p90rsk That Are Inducible by MAPK, J. Bioi. Chem., vol. 273, No. 3, pp. 1496-1505 (1998).
Datta et al. "Akt phosphorylation of BAD couples survival signals to the cell-intrinsic death machinery," Cell vol. 91, No. 2, pp. 231-241 (1997).
Franke et al. "PI3K: downstream AKTion blocks apoptosis." Cell, vol. 88, No. 4, pp. 435-437 (1997).
Fukunaga et al. "MNK1, a new MAP kinase-activated protein kinase, isolated by a novel expression screening method for identifying protein kinase substrates." The EMBO J., vol. 16, No. 8, pp. 1921-1933 (1997).
Hamaguchi et al. "Phosphorylation of cellular proteins in Rous sarcoma virus-infected cells: analysis by use of anti-phosphotyrosine antibodies," Molecular & Cellular Biology, vol. 8, No. 8, pp. 3035-3042 (1988).
Heffetz et al. Method. Enzymol., "Generation and use of antibodies to phosphothreonine", vol. 201, pp. 44-53 (1991).
Glenney et al. J Immun. Methods, "Monoclonal antibodies to phosphotyrosine", vol. 109, pp. 277-285 (1988).
Harlow et al. "Antibody-Antigen Interactions: Structure of the antibody-antigen complex," A Laboratory Manual, pp. 24-27, Cold Spring Harbor Laboratory Press (1999).
Harlow et al. Antibodies: A Laboratory Manual, Chapter 5, pp. 72-77, Cold Spring Harbor Laboratory Press (1988).
Hebbes et al. "A 'minimal epitope' anti-protein antibody that recognizes a single modified amino acid," Molecular Immunology, vol. 26, No. 9, pp. 865-873 (1989).
Khachigian et al. "A crossreactive antipeptide monoclonal antibody with specificity for lysyl-lysine," Journal of Immunological Methods, vol. 140, No. 2, pp. 249-258 (1991).
Kolle et al. "Substrate and sequential site specificity of cytoplasmic histone acetyltransferases of maize and rat-liver," Febs. Lett, vol. 421, pp. 109-114 (1998).
Kuby, Immunology, 3rd Ed. pp. 92-96, Freeman & Co. (1998).
Huse et al. Science, "Generation of a large combinatorial library of the immunoglobulin repertoire in phage lambda", vol. 246, pp. 1275-1281 (1989).
Imhof et al. Curr. Biol., "Acetylation of general transcription factors by histone acetyltransferases", vol. 7, pp. 689-692 (1997).

Kamps "Generation and Use of Anti-Phosphotyrosine Antibodies for Immunoblotting," Methods in Enzymology, vol. 201, pp. 101-111 (1991).
Antibodies: A Laboratory Manual, Chapter 5, pp. 72-77, Cold Spring Harbor Laboratory Press, eds. Harlow et al. (1988).
Antibodies: A Laboratory Manual, Cold Spring Harbor Laboratory Press, eds. Harlow et al. (1988).
Blume-Jensen et al, "Oncogenic kinase signaling", Nature, vol. 411, pp. 355-365, (2001).
Brumell et al, "Regulation of Src Homology 2-containing Tyrosine Phosphatase 1 during Activation of Human Neutrophils", Cell Biology and Metabolism, vol. 272, No. 2, pp. 875-882, Jan. 1997.
Chirica et al, "Fritless Capillary Columns for HPLC and CEC Prepared by Immobilizing the Stationary Phase in an Organic Polymer Matrix", Anal. Chem., vol. 72, No. 15, pp. 3605-3610, Aug. 1, 2000.
Conrads et al, "An enriched look at tyrosine phosphorylation", Nature Biotechnology, vol. 23, No. 1, pp. 36-37, Jan. 2005.
Cowley et al, "Activation of MAP kinase kinase is necessary and sufficient for PC12 differentiation and for transformation of NIH 3T3 cells", Cell, vol. 77, No. 6, pp. 841-852, Jun. 17, 1994.
De Corte et al, "Identification of Tyr438 as the major in vitro c-Src phosphorylation site in human gelsolin: A mass spectrometric approach", Protein Science, vol. 8, pp. 234-241, Aug. 24, 1998.
Dourtoglou et al, "O-Benzotriazolyl-N,N,N',N'-tetramethyluronium hexafluorophosphate as coupling reagent for the synthesis of peptides of biological interest", Synthesis, No. 7, pp. 572-574, (1984).
Erdjument-Bromage et al, "Examination of micro-tip reversed-phase liquid chromatographic extraction of peptide pools for mass spectrometric analysis", Journal of Chromatography A, vol. 826, No. 2, pp. 167-181, Nov. 27, 1998.
Fields et al, "HBTU activation for automated Fmoc solid-phase peptide synthesis.", Peptide Research, vol. 4, No. 2, pp. 95-101, Mar. 1, 1991.
Frackelton et al, "[8] Generation of monoclonal antibodies against phosphotyrosine and their use for affinity purification of phosphotyrosine-containing proteins", Methods in Enzymology, vol. 201, pp. 79-92, (1991).
Gaitlin et al, "Protein Identification at the Low Femtomole Level from Silver-Stained Gels Using a New Fritless Electrospray Interface for Liquid Chromatography—Microspray and Nanospray Mass Spectrometry", Analytical Biochemistry, vol. 263, No. 1, pp. 93-101, Oct. 1, 1998.
Gielbert et al. "Immunoaffinity Extraction Liquid Chromatography Mass Spectrometry with Monolithic Supports," Abstract MP A: 029, 50th ASMS Conference on Mass Spectometry and Allied Topics (2002).
Glenney, "[9] Isolation of tyrosine-phosphorylated proteins and generation of monoclonal antibodies", Methods in Enzymology, vol. 201, pp. 92-100, (1991).
Godovac-Zimmermann et al, "Functional proteomics of signal transduction by membrane receptors", Electrophoresis, vol. 20, Issue 4-5, pp. 952-961, Jan. 1, 1999.
Graves et al, "Protein Phosphorylation and Signal Transduction", Pharmacology & Therapeutics, vol. 82, No. 2-3, pp. 111-121, May-Jun. 1999.
Haley et al. "AACR Meeting Poster Presentation: Probing EGFr Signaling in HN5 Squamous Carcinoma Using the Duinazoline EGFr Inhibitor OSI-774 and Coupled Affinity Chromatography and Mass Spectrometry," www.aacr.org, (2001).
Hoffman et al, "Site-specific immobilization of antibodies by their oligosaccharide moieties to new hydrazide derivatized solid supports", Journal of Immunological Methods, vol. 112, No. 1, pp. 113-120, Aug. 9, 1988.
Shriver-Lake et al, "Antibody immobilization using heterobifunctional crosslinkers", Biosensors & Bioelectronics, vol. 12, No. 11, pp. 1101-1106, Jun. 9, 1997.
Kalo et al, "Multiple in Vivo Tyrosine Phosphorylation Sites in EphB Receptors", Biochemistry, vol. 38, No. 43, pp. 14396-14408, Oct. 5, 1999.
Kanner et al, "Immunoaffinity purification of tyrosine-phosphorylated cellular proteins", Journal of Immunological Methods, vol. 120, No. 1, pp. 115-124, Jun. 2, 1989.

(56) References Cited

OTHER PUBLICATIONS

Karin, "Signal transduction from the cell surface to the nucleus through the phosphorylation of transcription factors", Current Opinion in Cell Biology, vol. 6, No. 3, pp. 415-424, Jun. 1994.
Kearney et al, "New Mouse Myeloma Cell Line that Has Lost Immunoglobulin Expression but Permits the Construction of antibody-Secreting Hybrid Cell Lines", J. Immunol., vol. 123, No. 4, pp. 1548-1550, (1979).
Kennett, "Hybridomas: A new dimension in biological analyses", In Vitro, vol. 17, pp. 1036-1050, Dec. 1981.
Knorr et al, "New Coupling Reagents in Peptide Chemistry", Tetra. Lett., vol. 30, pp. 1927-1930 (1989).
Steen et al, "Detection of Tyrosine Phosphoryiated Peptides by Precursor Ion Scanning Quadrupole TOF Mass Spectrometry in Positive Ion Mode", Anal. Chem., vol. 73, No. 7, pp. 1440-1448 (2001).
Kozma et al, "Comparison of three methods for detecting tyrosine-phosphorylated proteins", Methods Enzymol., vol. 201, pp. 28-43 (1991).
Lewis et al, "Signal transduction through MAP kinase cascades", Adv. Cancer Res., vol. 74, pp. 49-139 (1998).
Mann et al, "Analysis of protein phosphorylation using mass spectrometry: deciphering the phosphoproteome", Trends in Biotechnology, vol. 20, No. 6, 8 pages, Jun. 2002.
Mann et al, "Analysis of Proteins and Proteomes by Mass Spectrometry", Annu. Rev. Biochem., vol. 70, pp. 437-473, (2001).
Mann, "Quantitative proteomics?", Nature Biotechnology, vol. 17, pp. 954-955, Oct. 1999.
Marcus et al, "Identification of platelet proteins separated by two-dimensional gel electrophoresis and analyzed by matrix assisted laser desorption/ionization-time of flight-mass spectrometry and detection of tyrosine-phosphorylated proteins", Electrophoresis, vol. 21, pp. 2622-2636, (2000).
New England BiolLabs, Inc./Cell Signaling Technology, Inc., "General Phospho-Ser/Thr/Tyr Antibodies", CST 2002 Catalog, http://www.neb.cadetail.nhn?id=9920, 10 pages, Feb. 1, 2002.
Novagen Novagen Technical Bulletin, "pET System Manual", 9th Edition (2000).
Ouyang et al, "Multi-site Phosphotyping of the ErbB-2 Oncoprotein in Human Breast Cancer", Molecular Diagnosis: A Journal Devoted to the Understanding of Human Disease Through the Clinical Application of Molecular Biology, vol. 6, No. 1, pp. 17-25 (2001).
Pandey et al, "Identification of a Novel Immunoreceptor Tyrosine-based Activation Motif-containing Molecule, STAM2, by Mass Spectrometry and Its Involvement in Growth Factor and Cytokine Receptor Signaling Pathways", The Journal of Biological Chemistry, vol. 275, No. 49, pp. 38633-38639, Dec. 8, 2000.
Tomaino et al, "Phosphopeptide Detection by a Data-depedent, Neutral-loss Driven MS3 Scan Usin Ion Trap Mass Spectrometry", 50th ASMS Conference on Mass Spectrometry and Allied Topics, Abstract ThOE 3:00 (2002).
Patton, "Detection technologies in proteome analysis", Journal of Chromotography B, vol. 771, pp. 3-31, (2002).
Peters et al, "Exploring the Phosphoproteome with Mass Spectrometry", Mini-Rev. Med. Chem., vol. 4, pp. 313-324 (2004).
Posewitz et al, "Immobilized Gallium (III) Affinity Chromatography of Phosphopeptides", Anal, Chem., vol. 71, No. 14, pp. 2883-2892 (1999).
Prat et al, "Bradykinin B1 Receptor Expression and Function on T Lymphocytes in Active Multiple Sclerosis", Neurology, vol. 53, pp. 2087-2092 (1999).
Quadroni et al, "Proteomics in Functional Genomics", Review, vol. 88, pp. 199-213 (2000).
Raggiaschi et al, "Phosphoproteome Analysis", Bioscience Reports, vol. 25, Nos. 1/2, pp. 33-44, Feb./Apr. 2005.
Raska et al, "Direct MALDI-MS/MS of Peptides Bound to Affinity media", Abstract WPA 034, 50th ASMS Conference on Mass Spectrometry and Allied Topics (2002).
Reinders et al, "State-of-the-art in phosphoproteomics", Proteomics, vol. 5, pp. 4052-4061, Feb. 15, 2005.
Schlom, "Monoclonal antibodies: they're more or less what you think," ed. Broder, Molecular Foundations of Oncology, pp. 95-134 (1991).
Upstate Biotechnology 2001 Catalog, p. 221.
Wang, "Generation and use of anti-phosphotyrosine antibodies raised against bacterially expressed abl protein", Methods Enzymol., vol. 201, pp. 53-65 (1991).
Wettenhall et al, "[15] Solid-phase sequencing of 32P-labeled phosphopeptides at picomole and subpicomole levels", Methods in Enzymology, vol. 201, pp. 186-199, (1991).
White et al, "[7] Preparation and use of anti-phosphotyrosine antibodies to study structure and function of insulin receptor", Methods in Enzymology, vol. 201, pp. 65-79, (1991).
Wirth et al, "The rat liver epithelial (RLE) cell nuclear protein database", Electrophoresis, vol. 14, No. 1, pp. 1199-1215, (1993).
Yanagida et al, "Matrix assisted laser desorption/ionization-time of flight-mass spectrometry analysis of proteins detected by anti-phosphotyrosine antibody on two-dimensional-gels of fibrolast cell lysates after tumor necrosis factor-α stimulation", Electrophoresis, vol. 21, No. 9, pp. 1890-1898, May 1, 2000.
Yates, III. et al. "SEQUEST," www.scripps.edu, 1 page (1999).
Yu et al, "Epitope mapping of monoclonal antibodies by mass spectrometry: Identification of protein antigens in complex biological systems", Journal of the American Society for Mass Spectrometry, vol. 9, pp. 208-215, Mar. 1998.

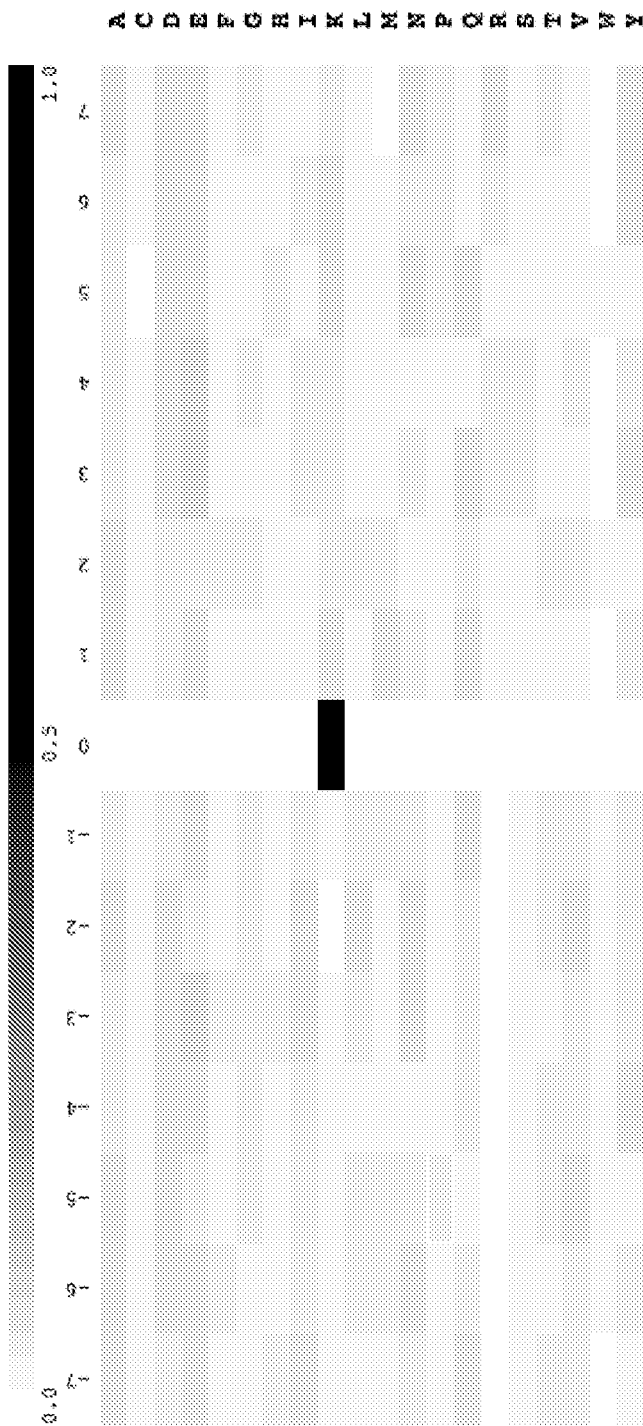
Figure 2: Heat map of ubiquitination peptides from MS

SEQUENCE LISTING

<160> NUMBER OF SEQ ID NOS: 30

<210> SEQ ID NO 1
<211> LENGTH: 471
<212> TYPE: PRT
<213> ORGANISM: Artificial Sequence
<220> FEATURE:
<223> OTHER INFORMATION: Synthetic Peptide

<400> SEQUENCE: 1

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Thr Ser Leu Thr Leu Thr Cys Thr Ala Ser Gly Phe Thr Ile Ser
        35                  40                  45

Ser Asn Tyr Tyr Ile Tyr Trp Val Arg Gln Ala Pro Gly Lys Gly Leu
    50                  55                  60

Glu Trp Ile Ala Cys Ile Tyr Gly Gly Ser Ser Gly Thr Thr Leu Tyr
65                  70                  75                  80

Ala Ser Trp Ala Lys Gly Arg Phe Thr Ile Ser Lys Thr Ser Ser Thr
                85                  90                  95

Thr Val Thr Leu Lys Met Pro Ser Leu Thr Ala Asp Thr Ala Thr
                100                 105                 110

Tyr Phe Cys Ala Arg Asp Phe Arg Gly Ala Asp Tyr Ser Ser Tyr Asp
            115                 120                 125

Arg Ile Trp Asp Thr Arg Leu Asp Leu Trp Gly Gln Gly Thr Leu Val
        130                 135                 140

Thr Val Ser Ser Gly Gln Pro Lys Ala Pro Ser Val Phe Pro Leu Ala
145                 150                 155                 160

Pro Cys Cys Gly Asp Thr Pro Ser Ser Thr Val Thr Leu Gly Cys Leu
                165                 170                 175

Val Lys Gly Tyr Leu Pro Glu Pro Val Thr Val Thr Trp Asn Ser Gly
            180                 185                 190

Thr Leu Thr Asn Gly Val Arg Thr Phe Pro Ser Val Arg Gln Ser Ser
        195                 200                 205

Gly Leu Tyr Ser Leu Ser Ser Val Val Ser Val Thr Ser Ser Ser Gln
    210                 215                 220

Pro Val Thr Cys Asn Val Ala His Pro Ala Thr Asn Thr Lys Val Asp
225                 230                 235                 240

Lys Thr Val Ala Pro Ser Thr Cys Ser Lys Pro Thr Cys Pro Pro Pro
                245                 250                 255

Glu Leu Leu Gly Gly Pro Ser Val Phe Ile Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Asp Asp Pro Glu Val Gln Phe Thr Trp Tyr Ile Asn
    290                 295                 300

Asn Glu Gln Val Arg Thr Ala Arg Pro Pro Leu Arg Glu Gln Gln Phe
305                 310                 315                 320

Asn Ser Thr Ile Arg Val Val Ser Thr Leu Pro Ile Ala His Gln Asp
                325                 330                 335

Trp Leu Arg Gly Lys Glu Phe Lys Cys Lys Val His Asn Lys Ala Leu
            340                 345                 350

Pro Ala Pro Ile Glu Lys Thr Ile Ser Lys Ala Arg Gly Gln Pro Leu
```

```
                355                 360                 365
Glu Pro Lys Val Tyr Thr Met Gly Pro Pro Arg Glu Glu Leu Ser Ser
370                 375                 380

Arg Ser Val Ser Leu Thr Cys Met Ile Asn Gly Phe Tyr Pro Ser Asp
385                 390                 395                 400

Ile Ser Val Glu Trp Glu Lys Asn Gly Lys Ala Glu Asp Asn Tyr Lys
                405                 410                 415

Thr Thr Pro Ala Val Leu Asp Ser Asp Gly Ser Tyr Phe Leu Tyr Ser
            420                 425                 430

Lys Leu Ser Val Pro Thr Ser Glu Trp Gln Arg Gly Asp Val Phe Thr
        435                 440                 445

Cys Ser Val Met His Glu Ala Leu His Asn His Tyr Thr Gln Lys Ser
    450                 455                 460

Ile Ser Arg Ser Pro Gly Lys
465                 470

<210> SEQ ID NO 2
<211> LENGTH: 238
<212> TYPE: PRT
<213> ORGANISM: Artificial Sequence
<220> FEATURE:
<223> OTHER INFORMATION: Synthetic Peptide

<400> SEQUENCE: 2

Met Asp Met Arg Ala Pro Thr Gln Leu Leu Gly Leu Leu Leu Leu Trp
1               5                   10                  15

Leu Pro Gly Val Thr Phe Ala Ala Val Leu Thr Gln Thr Pro Ser Pro
            20                  25                  30

Val Ser Ala Ala Val Gly Gly Thr Val Ser Ile Ser Cys Gln Ser Ser
        35                  40                  45

Glu Asn Val Tyr Asn Lys Asn Trp Leu Ser Trp Tyr Gln Gln Lys Pro
    50                  55                  60

Gly Gln Pro Pro Lys Leu Leu Ile Gln Lys Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Ala Asp Ala Ala Thr Tyr Tyr Cys
            100                 105                 110

Ala Gly Asp Tyr Gly Gly Thr Gly Asp Ala Phe Val Phe Gly Gly Gly
        115                 120                 125

Thr Glu Val Val Val Lys Gly Asp Pro Val Ala Pro Thr Val Leu Ile
130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235
```

```
<210> SEQ ID NO 3
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 3

Gly Phe Thr Ile Ser Ser Asn Tyr Tyr Ile Tyr Trp Val
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 4

Cys Ile Tyr Gly Gly Ser Ser Gly Thr Thr Leu Tyr Ala Ser Trp Ala
1               5                   10                  15

Lys Gly

<210> SEQ ID NO 5
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 5

Asp Phe Arg Gly Ala Asp Tyr Ser Ser Tyr Asp Arg Ile Trp Asp Thr
1               5                   10                  15

Arg Leu Asp Leu
            20

<210> SEQ ID NO 6
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 6

Gln Ser Ser Glu Asn Val Tyr Asn Lys Asn Trp Leu Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Lys Ala Ser Thr Leu Ala Ser
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 8
```

```
Ala Gly Asp Tyr Gly Gly Thr Gly Asp Ala Phe Val
1               5                   10
```

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

```
Met Gln Ile Phe Val Lys Thr Leu Thr Gly Lys
1               5                   10
```

<210> SEQ ID NO 10
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 10

```
Thr Leu Thr Gly Lys Thr Ile Thr Leu Glu Val Glu Pro Ser Asp Thr
1               5                   10                  15

Ile Glu Asn Val Lys
            20
```

<210> SEQ ID NO 11
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 11

```
Thr Leu Thr Gly Lys Thr Ile Thr Leu Glu Val Glu Pro Ser Asp Thr
1               5                   10                  15

Ile Glu Asn Val Lys Ala Lys
            20
```

<210> SEQ ID NO 12
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 12

```
Thr Ile Thr Leu Glu Val Glu Pro Ser Asp Thr Ile Glu Asn Val Lys
1               5                   10                  15

Ala Lys Ile Gln Asp Lys Glu Gly Ile Pro Pro Asp Gln Gln Arg
            20                  25                  30
```

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

```
Ala Lys Ile Gln Asp Lys Glu Gly Ile Pro Pro Asp Gln Gln Arg
1               5                   10                  15
```

<210> SEQ ID NO 14

```
<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 14

Ala Lys Ile Gln Asp Lys Glu Gly Ile Pro Pro Asp Gln Gln Arg
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 15

Ile Gln Asp Lys Glu Gly Ile Pro Pro Asp Gln Gln Arg
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Ala Lys Ile Gln Asp Lys Glu Gly Ile Pro Pro Asp Gln Gln Arg
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Ala Lys Ile Gln Asp Lys Glu Gly Ile Pro Pro Asp Gln Gln Arg
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 18

Leu Ile Phe Ala Gly Lys Gln Leu Glu Asp Gly Arg
1               5                   10

<210> SEQ ID NO 19
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 19

Leu Ile Phe Ala Gly Lys Gln Leu Glu Asp Gly Arg Thr Leu Ser Asp
1               5                   10                  15

Tyr Asn Ile Gln Lys
                20
```

```
<210> SEQ ID NO 20
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 20

Leu Ile Phe Ala Gly Lys Gln Leu Glu Asp Gly Arg Thr Leu Ser Asp
1               5                   10                  15

Tyr Asn Ile Gln Lys Glu Ser Thr Leu His Leu Val Leu Arg
            20                  25                  30

<210> SEQ ID NO 21
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 21

Thr Leu Ser Asp Tyr Asn Ile Gln Lys Glu Ser Thr Leu His Leu Val
1               5                   10                  15

Leu Arg

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 22

Val Tyr Ala Xaa Pro
1               5

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid

<400> SEQUENCE: 23

Cys Xaa Xaa Ala Xaa Val Ile Tyr Ala Ala Pro Phe Xaa Xaa Xaa
1               5                   10                  15

<210> SEQ ID NO 24
<211> LENGTH: 6
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 24

Thr Pro Xaa Xaa Ser Pro
1               5

<210> SEQ ID NO 25
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (11)..(16)
<223> OTHER INFORMATION: Xaa can be any naturally occurring amino acid

<400> SEQUENCE: 25

Cys Xaa Xaa Xaa Xaa Xaa Xaa Lys Gly Gly Xaa Xaa Xaa Xaa Xaa Xaa
1               5                   10                  15

<210> SEQ ID NO 26
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (4)..(4)
<223> OTHER INFORMATION: Xaa can be Lys or Arg

<400> SEQUENCE: 26

Ser Pro Arg Xaa
1

<210> SEQ ID NO 27
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (2)..(2)
<223> OTHER INFORMATION: Xaa can be Thr or Ser
<220> FEATURE:
<221> NAME/KEY: VARIANT
<222> LOCATION: (4)..(4)
<223> OTHER INFORMATION: Xaa can be Asp or Glu

<400> SEQUENCE: 27

Leu Xaa Gln Xaa
1

<210> SEQ ID NO 28
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
```

```
<222> LOCATION: (4)..(4)
<223> OTHER INFORMATION: Xaa can be Asp or Glu

<400> SEQUENCE: 28

Leu Thr Gln Xaa
1

<210> SEQ ID NO 29
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (4)..(4)
<223> OTHER INFORMATION: Xaa can be Asp or Glu

<400> SEQUENCE: 29

Leu Ser Gln Xaa
1

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (3)..(3)
<223> OTHER INFORMATION: Xaa is phosphotyrosine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 30

Val Ile Xaa Ala Xaa Pro
1               5
```

ANALYSIS OF UBIQUITINATED POLYPEPTIDES

CROSS-REFERENCE TO RELATED APPLICATIONS

This application is a continuation-in-part of U.S. Ser. No. 11/484,485, filed on Jul. 11, 2006, and is also a continuation-in-part of U.S. Ser. No. 13/856,933, filed on Apr. 4, 2013, which is a divisional of U.S. Ser. No. 12/967,284, filed on Dec. 14, 2010, which claims the benefit of U.S. Provisional Ser. No. 61/286,486, filed on Dec. 15, 2009. The entire contents of the foregoing applications are incorporated by reference herein.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Jan. 11, 2022, Apr. 30, 2021 is named "428510-000006.Sequence_Listing.txt" and is about 14.1 KB in size.

FIELD OF THE INVENTION

This invention provides methods, reagents and kits for analyzing polypeptides and their modifications from biological samples. In particular, the invention provides compositions, kits and methods for detecting ubiquitinated polypeptides and ubiquitination sites in proteins.

BACKGROUND

Protein ubiquitination is the one of the most common of all post-translational modifications. Ubiquitin is a highly conserved 76 amino acid protein which is linked to a protein target after a cascade of transfer reactions. Ubiquitin is activated through the formation of a thioester bond between its C-terminal glycine and the active site cysteine of the ubiquitin activating protein, E1 (Hershko, 1991, Trends Biochem. Sci. 16(7): 265-8). In subsequent trans-thiolation reactions, Ubiquitin is transferred to a cysteine residue on a ubiquitin conjugating enzyme, E2 (Hershko, et al., 1983, J. Biol. Chem. 267: 8807-8812). In conjunction with E3, a ubiquitin polypeptide ligase, E2 then transfers ubiquitin to a specific polypeptide target (see, e.g., Scheffner, et al., 1995, Nature 373(6509): 81-3), forming an isopeptide bond between the C-terminal glycine of ubiquitin and the δ-amino group of a lysine present in the target (See FIG. 1).

The covalent attachment of ubiquitin to cellular polypeptides, in most cases, marks them for degradation by a multi-polypeptide complex called a proteasome. The ubiquitin proteasome system is the principal mechanism for the turnover of short-lived polypeptides, including regulatory polypeptides (Weissman, 2001, Nat. Rev. Mol. Cell. Biol. 2: 169-78). Some known targets of ubiquitination include: cyclins, cyclin-dependent kinases (CDK's), NFKB, cystic fibrosis transduction receptor, p53, ornithine decarboxylase (ODC), 7-membrane spanning receptors, Cdc25 (phosphotyrosine phosphatase), Rb, Ga, c-Jun and c-Fos. Polypeptides sharing consensus sequences such as PEST sequences, destruction boxes, and F-boxes generally are also targets for ubiquitin-mediated degradation pathways (see, e.g., Rogers, et al., 1986, Science 234: 364-368; Yamano, et al., 1998, The EMBO Journal 17: 5670-5678; Bai, et al., 1996, Cell 86: 263-274).

Ubiquitin has been implicated in a number of cellular processes including: signal transduction, cell-cycle progression, receptor-mediated endocytosis, transcription, organelle biogenesis, spermatogenesis, response to cell stress, DNA repair, differentiation, programmed cell death, and immune responses (e.g., inflammation). Ubiquitin also has been implicated in the biogenesis of ribosomes, nucleosomes, peroxisomes and myofibrils. Thus, ubiquitin can function both as signal for polypeptide degradation and as a chaperone for promoting the formation of organelles (see, e.g., Fujimuro, et al., 1997, Eur. J. Biochem. 249: 427-433).

Deregulation of ubiquitination has been implicated in the pathogenesis of many different diseases. For example, abnormal accumulations of ubiquitinated species are found in patients with neurodegenerative diseases such as Alzheimer's as well as in patients with cell proliferative diseases, such as cancer (see, e.g., Hershko and Ciechanover, 1998, Annu Rev. Biochem. 67: 425-79; Layfield, et al., 2001, Neuropathol. Appl. Neurobiol. 27:171-9; Weissman, 1997, Immunology Today 18(4): 189).

SUMMARY

In accordance with the present invention, there is provided a method of producing antibodies that selectively recognize a plurality of peptides or proteins within a genome that contain the same short motif. Motif-specific antibodies of the invention therefore recognize the motif highly independent of the surrounding amino acid, peptide, or protein sequences. The method allows the production of motif-specific, context-independent antibodies that recognize single modified amino acids, for example phosphorylated serine, threonine, and tyrosine, or acetylated lysine, as well other unmodified or modified short motifs of multiple invariant amino acids.

The method encompasses the production and purification of highly context-independent antibodies that recognize specific and highly degenerate amino acid motifs common to multiple peptides or proteins within a genome, such as those found in kinase consensus sequences or other enzyme binding sites. Motifs recognized by the antibodies of the invention typically comprise one to six invariant amino acids. Furthermore, the method can be used to produce highly context-independent polyclonal or monoclonal antibodies.

Antibodies produced by the method of the present invention may be specific to virtually any desired recurring protein motif, either modified or unmodified. In preferred embodiments, the motif includes at least one modified amino acid, such as a phosphorylated, methylated, or glycosylated amino acid. For example, the method can be used to produce antibodies recognizing phosphothreonine alone or phosphothreonine together with several invariant amino acids in a motif, such as found in MAPK substrates, 14-3-3 binding proteins, or CDK consensus phosphorylation sites. It can also be used to produce antibodies specific for other modified amino acids, for example, acetylated lysine or nitrotyrosine, or to detect any short non-unique motif of one or more amino acids, in a highly context-independent fashion. Alternatively, the antibodies may be specific for unmodified motifs, such as those found in protein cleavage motifs, e.g. caspase cleavage motifs.

The invention also provides motif-specific, context-independent antibodies that specifically recognize short motifs comprising all or part of the following: MAPK consensus substrate motifs, CDK consensus substrate motifs, PKA consensus substrate motifs, Akt consensus substrate motifs, PKC consensus substrate motifs, ATM consensus substrate motifs, 14-3-3 consensus binding motifs, PDK1 consensus docking motifs, phosphothreonine-X-(arginine(R)/lysine (K)), PKC Zeta consensus substrate motifs, ABL kinase consensus substrate motifs, insulin receptor consensus substrate motifs, PI3K P85 consensus binding motifs, CaMKII consensus substrate motifs, SRC kinase consensus substrate motifs, CDC2/CDK2 consensus substrate motifs, GSK3 kinase consensus substrate motifs, and proline (P)-(phosphoserine/phosphothreonine)-proline (P). The antibodies of the invention are not limited, however, to these exemplary motifs, and other preferred species of modified motifs within the scope of the invention are described in more detail below.

The present invention further provides a method of profiling large and diverse protein populations on a genome-wide scale by utilizing motif-specific, context-independent antibodies against motifs conserved on such proteins. For example, phosphorylation-specific antibodies allow genome-wide profiling of changes in protein phosphorylation as a result of drug treatment.

The present invention also provides a method of identifying an unknown substrate of a known enzyme through the use of motif-specific, context-independent antibodies which are raised against motifs common to other substrates of the enzyme.

The use of such motif-specific, context-independent antibodies as a reagent for the detection of enzymatic modifications of a given motif within a substrate is also encompassed by the present invention.

One aspect of the invention relates to a method for determining the presence of at least one ubiquitinated polypeptide in a biological sample comprising: Contacting the sample with at least one hydrolyzing agent, wherein the hydrolyzing agent is capable of cleaving a ubiquitinated polypeptide to produce at least one ubiquitin remnant peptide, to obtain a hydrolyzed sample; Contacting the hydrolyzed sample with a substrate comprising an at least one immobilized binding partner; wherein the at least one immobilized binding partner preferentially binds a ubiquitin remnant peptide over a peptide having the same amino acid sequence as the ubiquitin remnant peptide but lacking a ubiquitin remnant; Removing the hydrolyzed sample from the substrate in a manner such that the at least one ubiquitin remnant peptide would remain bound to the immobilized binding partner; Contacting the substrate with an elution solution, wherein the least one ubiquitin remnant peptide would dissociate from the immobilized binding partner into the elution solution; and Determining the presence of a least one ubiquitinated polypeptide in the biological sample when the elution solution contains the at least one least ubiquitin remnant peptide.

In one embodiment of this aspect of the invention the determining is performed by LC, MS and preferably LC-MS/MS. In a further embodiment, the amino acid sequence of at least one ubiquitin remnant peptide present in the elution solution, is determined. In yet another embodiment, the sequence is compared to the sequence of the ubiquitinated polypeptide and the site of ubiquitination in the ubiquitinated polypeptide is thereby determined. In still a further embodiment, the elution solution further comprises at least one standard peptide, wherein the at least one standard peptide has the substantially same amino acid sequence as the at least one distinct peptide but a different measured accurate mass.

Another aspect of the invention relates to an isolated antibody that preferentially binds a ubiquitin remnant peptide over a peptide having the same amino acid sequence as the ubiquitin remnant peptide but lacking a ubiquitin remnant. In one embodiment, the antibody is a monoclonal antibody. In another embodiment, the antibody is a polyclonal antibody. In still yet another embodiment, the antibody is selected from the group consisting of single chain Fvs (scFvs), Fab fragments, Fab' fragments, F(ab') 2, disulfide linked Fvs (sdFvs), Fvs, and fragments thereof. In yet another embodiment, the antibody comprises a polypeptide of SEQ ID NO: 1. In a further embodiment, the antibody comprises a polypeptide of SEQ ID NO: 2. In yet another embodiment, the antibody comprises a light chain polypeptide of SEQ ID NO: 2 and a heavy chain polypeptide of SEQ ID NO: 1. In still another embodiment, the antibody comprises an antigen binding site comprising the variable region of the heavy chain set forth in SEQ ID NO: 1. In still a further embodiment, the antibody comprises an antigen binding site comprising the variable region of the light chain set forth in SEQ ID NO: 2.

Another aspect of the invention relates to an isolated nucleic acid encoding an antibody that preferentially binds a ubiquitin remnant peptide over a peptide having the same amino acid sequence as the ubiquitin remnant peptide but lacking a ubiquitin remnant.

A further aspect of the invention relates to a cell comprising a nucleic acid, preferably in the form of a vector, that encodes an antibody that preferentially binds a ubiquitin remnant peptide over a peptide having the same amino acid sequence as the ubiquitin remnant peptide but lacking a ubiquitin remnant.

Yet a further aspect of the invention relates to a method for determining whether a patient is has or is likely to have or develop a disease associated with a least one ubiquitinated polypeptide comprising: obtaining a biological sample from the patient; Contacting the sample with at least one hydrolyzing agent, wherein the hydrolyzing agent is capable of cleaving a ubiquitinated polypeptide to produce at least one ubiquitin remnant peptide, to obtain a hydrolyzed sample; Contacting the hydrolyzed sample with a substrate comprising an at least one immobilized binding partner; wherein the at least one immobilized binding partner preferentially binds a ubiquitin remnant peptide over a peptide having the same amino acid sequence as the ubiquitin remnant peptide but lacking a ubiquitin remnant; Removing the hydrolyzed sample from the substrate in a manner such that the at least one ubiquitin remnant peptide would remain bound to the immobilized binding partner; Contacting the substrate with an elution solution, where in the least one ubiquitin remnant peptide would dissociate from the immobilized binding partner into the elution solution; and Determining the presence of a least one ubiquitinated polypeptide in the biological sample when the elution solution contains the at least one least ubiquitin remnant peptide; Determining that the patient is has or is likely to have or develop the disease associated with a least one ubiquitinated polypeptide if the least one ubiquitinated polypeptide is present in the biological sample.

Another aspect of the invention relates to a method for determining whether a disease is associated with at least one ubiquitinated polypeptide comprising Obtaining a biological sample from a patient having the disease; Contacting the sample with at least one hydrolyzing agent, wherein the hydrolyzing agent is capable of cleaving a ubiquitinated polypeptide to produce at least one ubiquitin remnant peptide, to obtain a hydrolyzed sample; Contacting the hydrolyzed sample with a substrate comprising an at least one immobilized binding partner; wherein the at least one immobilized binding partner preferentially binds a ubiquitin remnant peptide over a peptide having the same amino acid sequence as the ubiquitin remnant peptide but lacking a ubiquitin remnant; Removing the hydrolyzed sample from the substrate in a manner such that the at least one ubiquitin remnant peptide would remain bound to the immobilized binding partner; Contacting the substrate with an elution solution, where in the least one ubiquitin remnant peptide would dissociate from the immobilized binding partner into the elution solution; Determining the presence of a least one ubiquitinated polypeptide in the biological sample when the elution solution contains the at least one least ubiquitin remnant peptide; and Determining that the disease is associated with the presence of the at least one ubiquitinated polypeptide if the least one ubiquitinated polypeptide is absent in the biological sample of a healthy individual.

Still another aspect of the invention relates to a method for determining whether a disease is associated with at least one ubiquitin remnant peptide Obtaining a biological sample from a patient having the disease to obtain a disease biological sample; Obtaining a biological sample from a healthy patient to obtains a healthy biological sample; Contacting the disease biological sample with at least one hydrolyzing agent, wherein the hydrolyzing agent is capable of cleaving a ubiquitinated polypeptide to produce the least one ubiquitin remnant peptide, to obtain a disease hydrolyzed sample; Contacting the healthy biological sample with at least one hydrolyzing agent, wherein the hydrolyzing agent is capable of cleaving a ubiquitinated polypeptide to produce the least one ubiquitin remnant peptide, to obtain a healthy hydrolyzed sample; Contacting the disease hydrolyzed sample with a substrate comprising an at least one immobilized binding partner; wherein the at least one immobilized binding partner preferentially binds a ubiquitin remnant peptide over a peptide having the same amino acid sequence as the ubiquitin remnant peptide but lacking a ubiquitin remnant; Removing the disease hydrolyzed sample from the substrate in a manner such that the at least one ubiquitin remnant peptide would remain bound to the immobilized binding partner; Contacting the substrate with an elution solution, where in the least one ubiquitin remnant peptide would dissociate from the immobilized binding partner into the elution solution; and Determining the presence of the a least one ubiquitin remnant peptide in the elution solution; Determining that the disease is associated with the presence of the at least one ubiquitin remnant peptide if the at least one ubiquitin remnant peptide is absent in the healthy biological sample.

United States patent application publications numbers 2007/0026261, 2011/0111424, and 2013/0245237 are specifically incorporated herein by reference for all purposes.

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited above are incorporated herein by reference in their entirety to the extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

BRIEF DESCRIPTION OF THE DRAWINGS

A more complete understanding of the present invention may be obtained by reference to the accompanying drawings, when considered in conjunction with the subsequent detailed description. The embodiments illustrated in the drawings are intended only to exemplify the invention and should not be construed as limiting the invention to the illustrated embodiments, in which:

FIG. 2 shows a heat map illustrating the frequency of amino acids found with the BL4936 polyclonal antibody in a study of four mouse tissues. Altogether 1458 non-redundant peptides were included in this frequency map. The map clearly shows there are no strongly preferred amino acids at least seven residues to the amino-terminal side of K(GG) modification sites (−7 to −1 in the figure) or at least seven residues to the carboxyl-terminal side of K(GG) modification sites.

DETAILED DESCRIPTION

Figure 1:
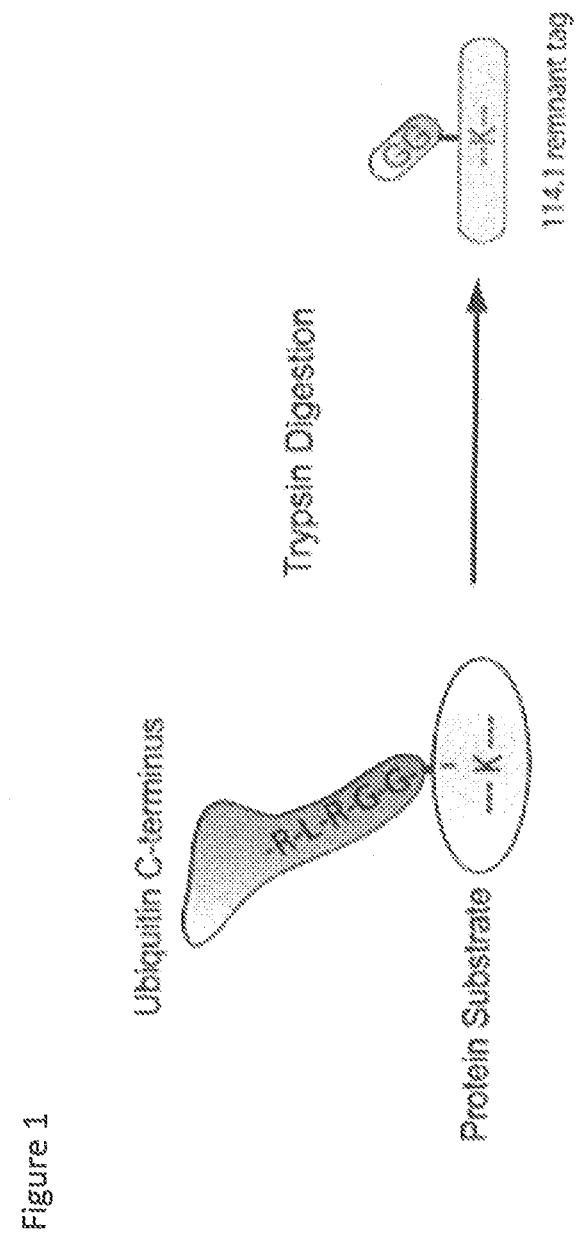
FIG. 1 depicts a cartoon of the formation of a ubiquitin remnant.

Immunizing a host with a degenerate peptide library comprising (i) a short fixed amino acid motif (the target motif) containing one or more invariant amino acids, and (ii) a plurality of degenerate amino acids representing many of the 19 amino acids (excepting cysteine) at positions flanking the motif will produce antibodies specific for all or part of the target motif and tolerant to many, if not all, amino acids at the degenerate (i.e. variable) positions flanking the fixed motif. Such antibodies will then react with the antigenic determinant (a motif consisting of all or part of the target motif) despite being presented in the context of a broad range of different surrounding amino acid, peptide, or protein sequences. The highly context-independent antibodies are thus capable of recognizing a plurality of peptides or proteins within a genome that contain the motif, typically consisting of 1-6 invariant amino acids together with one or more post-translationally modified amino acids. The produced antibody may be specific for a motif consisting of a part of the target motif that contains a modified residue, in which case the antibody will recognize peptides and proteins containing that part of the target motif, as well as proteins containing the entire target motif. The invariant residue(s) of the fixed target motif may be a single unmodified or modified amino acid, such as a phosphorylated or unphosphorylated residue, or may be multiple unmodified or modified amino acids, such as a consensus recognition site, comprising a short motif. These short motifs, unlike longer peptide sequences that represent unique protein sequences or sites, frequently serve as targets of enzymatic modification, such as single phosphorylatable residues or consensus substrate or consensus binding sites, which are common to multiple peptide or protein targets in a cell.

As used herein, "degenerate amino acids" means amino acid positions that are non-fixed and thus variant. The term includes amino acid positions that are highly degenerate, representing most, if not all, of the 20 amino acids at that position, positions that are moderately degenerate (i.e. biased towards certain of the 20 amino acids), and positions that are slightly degenerate, representing at least two different amino acids.

As used herein, "degenerate peptide library" means a peptide library comprising a plurality of individual peptides collectively containing one or more degenerate amino acids. The term includes a peptide library of any length suitable for use as an immunogen to raise anti-peptide antibodies, typically, but not limited to, about 6 to 20 amino acids.

As used herein, "flanking," with respect to the position of the motif in a peptide library, means to the side or sides of, and does not necessarily mean contiguous or adjacent to.

As used herein, "modified" amino acid as means any naturally-occurring (in vivo) post-translationally modified amino acid, including but not limited to phosphorylated, acetylated, glycosylated, methylated, and ubiquitinated amino acids. Modified amino acids may be singly modified or may contain multiple moieties of the same modification (e.g. doubly- or triply-acetylated arginine, doubly-methylated arginine). Reference to, e.g. "methylarginine" encompasses the various forms, e.g. monomethyl, dimethyl, of such modified amino acid.

As used herein, "motif" means a short amino acid sequence, typically comprising 1 to 6 invariant (i.e. non-degenerate) amino acids including at least one modified amino acid, which occurs in a plurality of peptides or proteins within a genome, and thus is recurring (non-unique). The term includes single amino acid motifs, such as phosphothreonine, and multiple amino acid motifs, such as comprised in kinase consensus substrate motifs, protein binding motifs, phosphatase motifs, or protein cleavage motifs. Motifs including multiple invariant amino acids may also comprise multiple variant (i.e. degenerate) amino acid positions. For example RXRXXT*, the Akt substrate consensus sequence motif, contains 3 invariant amino acids and 3 degenerate amino acids.

As used herein, "motif-specific, context-independent antibody" means an antibody which preferentially recognizes a plurality of peptides or proteins within a genome that contain the motif for which the antibody is specific; the specificity of the antibody is thus substantially independent of the surrounding protein or peptide context in which the antigenic motif occurs. Motif-specific, context-independent antibodies are thus suitable for genome-wide profiling applications, as the antibodies recognize many, if not most, of proteins within a genome containing the motif. The motif that the antibody preferentially binds may consist of all or part of the "target motif" presented in the immunizing degenerate peptide library, but in either case includes any modified amino acid(s) presented in the target motif.

As used herein, "substrate" means any target molecule, including peptides or proteins, which an enzyme specifically recognizes and acts upon.

The general method by which motif-specific, context-independent antibodies are produced in accordance with the present invention is as follows: Motif-specific antibodies that specifically recognize many different proteins or peptides containing a desired motif substantially independently of the amino acids flanking the motif may be obtained by constructing (e.g. synthesizing), for use as an immunogen, a degenerate peptide library comprising (i) a fixed target motif comprising one or more invariant amino acids, and (ii) a plurality of degenerate amino acids flanking the motif. In a preferred embodiment, the target motif includes at least one modified amino acid. For example, in one preferred embodiment, the library comprises XXXXXXJ*XXXXXXC where X=all 20 amino acids except cysteine, and the motif, J*,=a modified (*) amino acid (J), for example, phosphothreonine (T*) or acetylated-lysine (K*). The terminal cysteine is used to couple the library to a carrier, thus cysteine is excluded from the degenerate positions to avoid unwanted coupling. Other exemplary peptide libraries and motifs are set out in the Examples provided below (e.g. a degenerate library comprising (in place of the J* indicated above) the MAPK consensus substrate motif, PXS*P, is described in Example II). It will be appreciated that the specific target residue(s) of the motif may be unmodified and that a shorter or longer library may be generated and less than all of the degenerate amino acids flanking the motif may be varied.

It will be recognized that a peptide library of any length suitable for use as an immunogen to raise anti-peptide antibodies may be advantageously employed in the practice of the invention. The construction and typical range of length of such peptide antigens has been well described. See e.g., ANTIBODIES: A LABORATORY MANUAL, Harlow and Lane Eds., p. 75-76, Cold Spring Harbor Laboratory (1988); Czernik, supra. at 266-67. Generally, the length of suitable peptide antigen is only limited by the increasing cost and difficulty of synthesizing ever larger peptides, which do not appreciably improve antigenicity. Thus, in one embodiment, the peptide library of the invention is about 6 to 20 residues long. In another preferred embodiment, the peptide library is about 6 to 14 residues long. In still another preferred embodiment, the peptide library is about 6 to 18 residues long.

The peptide library may be constructed, as in a preferred embodiment, with most, if not all, of the amino acids flanking the motif being highly degenerate; the amino acids are those positions are any of the 19 amino acids (excepting cysteine). However, less highly degenerate libraries may alternatively be constructed to contain bias for or against certain residues at particular flanking amino acid positions, or in which less than all of the flanking amino acids are degenerate. For example, in another preferred embodiment, degenerate amino acids at positions flanking the motif may be any amino acid except cysteine (C) and tryptophan (W). Cysteine is excluded to avoid unwanted coupling, as discussed. Tryptophan is excluded because it is a rare amino acid generally, and rarely occurs in positions surrounding modification sites, such as phosphorylation sites, in proteins. Biasing the flanking amino acid positions against W is also believed to reduce the likelihood of generating any antibody response to W, which is a large and somewhat antigenic residue, thus focusing the antibody response of the host on the desired motif. Tyrosine (Y) may also be excluded for the same reason.

Similarly, certain flanking amino acid positions may be biased for particular residues to increase the antigenicity of the immunizing degenerate peptide library. In some cases, it may be known that a given motif adopts a certain structure, in vivo, that is influenced by the presence of particular amino acids surrounding that motif. In such cases, a degenerate peptide library may similarly be constructed with biased flanking residues in an effort to increase the immunogenicity of the fixed motif in the peptide library by introducing structure mimicking that found in vivo. For example, if desired, the influence of particular flanking residues may be determined in advance as follows: A library of peptides that contain a single modifiable target residue, such as phosphotyrosine, and varying flanking residues is constructed. The library is reacted with a desired enzyme, such as a particular kinase of interest, to modify the target residue. The modified peptides are then separated from any unmodified peptides, and batch-sequenced (e.g. by Edman degradation) to examine the abundance of each amino acid at a particular flanking position. An enriched amino acid at a particular flanking position indicates that residue is favored by the enzyme at that flanking position. (per personnel communication, Lewis Cantley). A degenerated peptide library may then be constructed with bias towards the favored residue(s) one or more flanking positions.

In a preferred embodiment, selected flanking amino acids may be biased in order to achieve about 50% representation of one or two amino acids at a given degenerate position in the peptide library and about 50% of all other amino acids except C and W represented at that position. This bias is introduced by biasing the coupling mixture for the desired position during synthesis, described below. By way of further example, in a preferred embodiment (see Example XV(b)), context-independent antibodies specific for the ABL kinase consensus substrate motif (VIY*AXP, where Y*=phosphotyrosine) (SEQ ID NO:30) may be produced by constructing a biased degenerate peptide library comprising CXXAXVIY*AAPFXXX (SEQ ID NO:23), where bold indicates invariant residues of the motif, X=any amino acid except C and W. and A and F=flanking positions biased 50% towards alanine (A) or phenylalanine (F), respectively (the other 50% representing any amino acid except C or W). Where bias towards two or more amino acids at a given degenerate position is desired, the coupling mixture for that position may be prepared with a total bias of 50% to the desired residues, collectively (e.g. total bias of 50% to K and R (in other words about 25% total bias to each of K and R). It will be recognized that a greater or lesser amount of bias (than 50%) may be advantageously employed. Further examples of such biased peptide libraries are provided in Example XV. It is also anticipated that a mixture of peptides corresponding to approximately 10 known kinase substrates sharing a common motif may be used as an immunogen to generate antibodies to the common motif that are somewhat context-independent.

The degenerate amino acids in the library, including those within or flanking the motif, may be varied at more than one position simultaneously, or, as in the preferred embodiment, varied at only one surrounding sequence position per degenerate molecule, such that a library is produced which is completely degenerate at every position except the fixed residue(s) of the motif. The peptide library can be synthesized by standard F-Moc solid phase peptide synthesis using an ABI peptide synthesizer and using mixtures of each amino acid during degenerate coupling reactions.

The target motif may consist of a single invariant amino acid (either modified or unmodified), or may comprise multiple amino acids, typically 1 to 6 invariant amino acids, representing a short motif common to a plurality of different peptides or proteins within a genome. The uniqueness of a particular peptide sequence is related to its length, since only one of twenty possible amino acids occurs at each position in the peptide chain. Thus, the probability of a sequence of length (n) occurring at random is $1/20$ raised to the nth power. By way of example, for a particular sequence of length 4 (i.e. 4 fixed residues of a motif) there are a total of $(20)^4=160,000$ possible amino acid sequence, hence the probability of this specific sequence occurring is $1/160,000=6.25\times10^{-6}$. For vertebrate genomes encoding approximately 90,000 proteins of an average length of 500 amino acids, there are approximately 30 million different amino acid sequences, so a 4 amino acid sequence motif would occur at random roughly $(90,000\times500)\times6.25\times10^{-6}=300$ times across the entire genome. Similarly, a 5 amino acid motif will occur about 15 times, a 6 amino acid motif will occur around once, and a 7 amino acid motif will occur about 0.05 times across the entire genome.

Thus, from this rough analysis, it is clear that an immunizing peptide sequence should generally be 7 amino acids or greater in length in order to generate an antibody with unique specificity (i.e. not reactive with any other human proteins). For precisely this reason, conventional site-specific peptide immunogens are typically 10-15 amino acids in length, which is small enough to focus the antibody response to the desired region of the protein, yet long enough to ensure multiple overlapping unique epitopes. See, e.g. ANTIBODIES: A LABORATORY MANUAL (1988), supra. Epitopes recognized by native immune system antibodies are typically even larger. Conversely, the range of motif length useful for generating conserved motifs across many proteins is between about 1 to 6 amino acids. This short range comports with both statistical prediction, as discussed above, and the observation that most, if not all, kinase consensus motifs reported to date comprise 6 or fewer invariant amino acids. See, e.g. L. Cantley, "Use of Peptide Libraries to Determine the Substrate Specificity of Protein Kinases," in Cell Signaling Technology, Inc.'s Catalogue and Technical Reference (2000-2001), p. 198; Songyang et al., Current Biology 4: 973-982 (1994); Songyang et al., Mol. Cell. Biol. 16:6486-6493 (1996); Nishilawa et al., J. Biol. Chem. 272: 952-960 (1990); Kemp et al., Trends Biochem. Sci. 15: 342-346 (1990); al-Obeid et al., Biopolymers 47:197-223 (1998); Yaffe et al., Nature Biotech. 19: 348-353 (2001); PROTEIN PHOSPHORYLATION: A PRACTICAL APPROACH, D. Hardie ed., p. 267, IRL Press (1993).

In preferred embodiments, the target motif comprises at least one modified amino acid, e.g. a phosphorylated amino acid. Alternatively, the motif may comprise multiple modified amino acids (e.g. T*PXXS*P (SEQ ID NO:24)), the GSK consensus substrate motif, comprises two phosphorylated residues). In other embodiments, the motif is an unmodified motif, such as protein cleavage motifs (e.g. caspase cleavage motifs). In certain preferred embodiments, the motif is a single phosphorylated amino acid, a single acetylated amino acid, or a single nitrosylated amino acid. Such preferred motifs include, but are not limited to, a single phosphothreonine, a single phosphoserine, a single phosphotyrosine, a single acetyl-lysine, and a single nitrotyrosine. In other preferred embodiments, the motif comprises at least two invariant amino acids including at least one phosphotyrosine or phosphothreonine, or comprises at least one phosphoserine but does not consist of phosphoserine-proline. Another preferred motif is phosphothreonine-X-arginine (T*XR). In other preferred embodiments, the motif comprises all or part of a kinase consensus substrate motif or a protein binding motif. Such preferred motifs include, but are not limited to, all of part of MAPK consensus substrate motifs, CDK consensus substrate motifs, PKA consensus substrate motifs, Akt consensus substrate motifs, PKC consensus substrate motifs, ATM consensus substrate motifs, 14-3-3 consensus binding motifs, and bulky-ring/PDK1 consensus docking motifs. In still other preferred embodiments, the motif comprises all or part of PKC Zeta consensus substrate motifs, ABL kinase consensus substrate motifs, CDK5 consensus substrate motifs, insulin receptor consensus substrate motifs, PI3K P85 consensus binding motifs, CaMKII consensus substrate motifs, Src kinase consensus substrate motifs, CDC2/CDK2 consensus substrate motifs, GSK3 kinase consensus substrate motifs, and proline-phosphoserine-proline (PS*P).

The incorporation of modified amino acids at invariant (i.e. fixed) positions within the motif in the peptide library should not be limited to phosphorylation or acetylations, as other modified protected amino acids can also be incorporated. For example, motifs comprising one or more amino acids modified with lipids (e.g. farnesylated, isoprenylated) or protected O-linked or N-linked sugars (e.g. glycosylated), methylated, or ribosylated amino acids, or nucleotides, polymers of nucleotides, nucleosides, or amino acids such as ubiquitin, or amino acid analogues may be advantageously employed in the invention. Amino acids modified with residues resulting from the cleavage of a post-translational modification (e.g. gly-gly addition resulting from cleavage of ubitquitin modification) are within the scope of the invention.

In order to produce as equal a representation of each non-excluded amino acid as possible at each degenerate position, several rounds of altering the amino acid composition, synthesizing, and peptide sequencing are conducted. Amino acid sequence analysis at several different positions along the peptide is conducted to verify a random amino acid representation at each position and that the random representation is maintained throughout the synthesis. It will be recognized by one of skill in the art that the number of rounds may vary in order to achieve an equal distribution of all amino acids at each position.

Alternatively, the representation of particular amino acids at certain degenerate positions in the peptide library may be intentionally biased, as discussed above. For example, in addition to exclusion of cysteine (C) (to avoid unwanted coupling), the rare residue tryptophan (W) may also be generally excluded at each degenerate position. Biasing the degenerate amino acids flanking the motif against W is believed to reduce the likelihood of generating any unwanted antibodies to W, a large, somewhat antigenic residue. Similarly, certain flanking amino acid positions may be biased for particular residues to increase the antigenicity of the immunizing degenerate peptide library, as discussed above. For example, in a preferred embodiment, selected flanking amino acids may be biased in order to achieve about 50% representation of one or two amino acids at a given degenerate position in the peptide library and about 50% of all other amino acids except C and W represented at that position. This bias is introduced at specific degenerate positions by biasing the coupling mixture for the desired position during synthesis, described below. It will be recognized that a greater or lesser amount of bias (than 50%) may be advantageously employed.

The degenerate peptide library is used as an antigen, preferably by covalent coupling to a carrier. In a preferred embodiment, keyhole limpet hemocyanin (KLH) emulsified in Freund's adjuvant is used as the coupling agent, and the coupled peptide library injected intradermally into a host, such as female New Zealand white rabbits, in order to raise context-independent antibodies specific for a motif consisting of all or part of the target motif, but in either case including the invariant modified residue(s) of the target motif. Antibodies of the invention include those specific for either the target motif itself (in which case the antibodies will not recognize peptides or proteins lacking the entire target motif) or for a part of the target motif (in which case the antibodies will recognize peptides or proteins containing only that part of the target motif, as well as those containing the entire target motif). In the latter case, the motif for which the antibody is specific consists of that part of the target motif that is antigenic. Booster injections may be given in incomplete Freund's adjuvant until an immune response is obtained. Antibody titre is measured by a suitable method, such as ELISA against the motif-specific peptide libraries. Antisera raised in this manner may be used in both crude or purified preparations, as outlined below.

For motifs containing invariant positions that may be two or three specific allowable residues, e.g. bulky ring/PDK1 docking motif ((F/Y) (T*/S*) or (S*/T*)F) and CDC2/CDK2 consensus substrate motif (S*PR(K/R)) (SEQ ID NO:26), a single degenerate peptide library will typically be constructed with a mixture of allowable residues at such positions, and then coupled to the carrier. Alternatively, however, more than one degenerate peptide library, each with only one of the allowable residues at such positions, may first be constructed, coupled to the carrier for immunization, and then the antisera from immunization with each library mixed together. By way of example, a degenerate peptide library comprising the ATM consensus substrate motif, L(T*/S*)Q(D/E) (SEQ ID NO:27), may be constructed as two distinct degenerate libraries, one comprising LT*Q(D/E) (SEQ ID NO:27) and the other LS*Q(D/E) (SEQ ID NO:27), which are used for immunization separately, and the antisera then mixed together (see, e.g., Example XIII).

Antisera from the most promising hosts are purified, for example over protein A, and adsorbed over a J (non-modified motif peptide library column. In a preferred embodiment, the nonadsorbed fraction (flow through) is then applied to a J* column (modified motif, eluted at suitable pH, dialyzed and tested for J* (modified motif specificity by a suitable method, such as ELISA using J* and J as antigen.

Antibodies affinity purified in this fashion recognize the J* (modified motif) peptide library but do not react with the J (unmodified motif library and exhibit a high degree of specificity for J*. These antibodies may be further tested for lack of reactivity against the unmodified form of the target motif (comprising modified amino acid(s), J*), or a J* homologue, utilizing a suitable method, such as ELISA.

Antibodies may be further tested, as in preferred embodiments, by western blotting or another suitable method, using cell extracts prepared from cells treated with and without a selected protein modification enzyme inhibitor, such as protein phosphatase inhibitor okadaic acid. Treatments that increase protein modification will increase the number of antibody reactive proteins as well as the intensity of reactivity. The J* (modified motif-specific antibodies will react with a relatively small number of proteins from control extracts but will react with a very large number following treatment with the selected inhibitor. The antibodies will show no reactivity with the inactive-non-modified versions of these proteins, demonstrating a high degree of J* specificity and suggesting broad cross-reactivity to many different proteins within a genome that contain the same modified motif.

The degree of context-independence may be more carefully examined, as in preferred embodiments, for example, by ELISA analysis against individual J* (modified motif peptides that are mixed together or tested individually. Such analysis can indicate if poor reactivity occurs with certain motifs, such as when J* (modified motif is followed by proline, for example.

The context-dependence of the J* (modified motif antibody recognition may be further examined, as in the preferred embodiment, using a immobilized grid of modified-peptide libraries. In addition to a fixed target motif, J*, each different library is synthesized to contain an additional fixed amino acid at different positions relative to J* but with all other positions containing all 20 amino acids except cysteine. Each peptide library is coated, for example, on the bottom of an ELISA well and exposed to the J* antibodies. Motif-specific antibodies that do not react with a particular spot (peptide library) on the grid do not bind when the specified amino acid is present at the specified position. This analysis determines whether or not a particular amino acid at a particular position relative to J* (modified motif will allow or block binding. Such testing aids in determining whether the antibody is specific for the entire target motif (presented in the degenerate peptide library) or for a part of the target motif, as discussed above. Such testing also confirms the context-independence of the antibody. For example, in a preferred embodiment, the invention provides a context-independent antibody that recognizes a motif consisting of a single phosphothreonine, where the specificity of the antibody is independent of variations in the amino acid residue at the −1 position relative to the motif, as determined by peptide grid (binding) analysis.

Alternatively, purified antibodies can be linked to beads, allowed to bind the modified or unmodified library, unbound sequences washed away, and bound sequences recovered and subject to amino acid sequencing to determine the amount of each amino acid present at each position in the library. This information will indicate what amino acids are tolerated at each position.

Monoclonal antibodies may be prepared, as in one form of the preferred embodiment, by coupling the J* (modified motif) degenerate peptide library to a suitable carrier, such as KLH, and injected into a host, such as BalbC mice, in order to raise antibodies specific for the target motif or part of the target motif. The J* peptide-KLH conjugate may be emulsified in Freund's adjuvant and booster injections in incomplete Freund's adjuvant may be carried out every other week until a response is obtained.

Antibody titre is measured by a suitable method, such as ELISA against J* (modified motif) and non-J* peptide libraries. Sera from hosts showing high-titre responses are adsorbed with immobilized non-J* peptide and the nonadsorbed fraction tested by, for example, western blotting.

Spleens from hosts showing J* (modified motif-specific responses are fused to myeloma cells and hybridoma clones are selected and screened. Supernatants from individual clones are screened first for their ability to bind the J*-peptide library. Positive clones are next screened for their cross-reactivity against the non-J* library. Clones showing the highest degree of J*-specificity are chosen for further analysis as described above in steps (5) through (8).

Overproduction of monoclonal antibodies resulting from step (11) above may be carried out, for example, by harvesting ascites, culturing selected hybridoma clones, or cloning into a host organism, such as *E. coli*.

The inventors have discovered antibody reagents that specifically bind peptides carrying a ubiquitin remnant from a digested or chemically treated biological sample. See also U.S. application Ser. No. 12/455,496 (which is incorporated by reference in its entirety for all purposes and without limitation).

These reagents allow the technician to identify ubiquitinated polypeptides as well as the sites of ubiquitination on them. The reagents are preferably employed in proteomic analysis using mass spectrometry. The antibody reagents (in both polyclonal and monoclonal form) specifically bind the remnant of ubiquitination, i.e., a diglycine modified epsilon amine of lysine left on a peptide which as been generated by digesting or chemically treating ubiquitinated proteins. The inventive antibody reagents' affinity to the ubiquitin remnant does not depend on the remaining amino acid sequences flanking the modified lysine, i.e., they are "context independent". In addition, the antibodies of the invention do not cross react with peptides lacking the ubiquitin remnant. See for example, U.S. Pat. Nos. 6,441,140; 6,982,318; 7,198,896; 7,259,022; 7,300,753; 7,344,714; U.S. Ser. No. 11,484,485, all herein incorporated by reference in their entirety.

Notwithstanding the low abundance of ubiquitinated polypeptides in biological samples, the invention allows for high-throughput MS identification of ubiquitination sites. Immunoaffinity purification (IAP) with the inventive antibodies enrich those ubiquitinated peptides derived from the ubiquitinated portion of polypeptides relative to peptides lacking ubiquitination sites, as well as peptides from proteins which strongly interact with ubiquitin or ubiquitinated proteins, thereby significantly reducing the complexity of the peptide mixture. The purified digest sample can be directly applied to tandem MS for efficient peptide sequence analysis and protein identification to reveal ubiquitinated polypeptides and their sites of ubiquitination.

Prior to describing various embodiments of the current invention, the following definitions are provided:

As used herein the term "peptide" or "polypeptide" refers to a polymer formed from the linking, in a defined order, of preferably, .alpha.-amino acids, D-, L-amino acids, and combinations thereof. The link between one amino acid residue and the next is referred to as an amide bond or a peptide bond. Proteins are polypeptide molecules (or having multiple polypeptide subunits). The distinction is that peptides are preferably short and polypeptides/proteins are preferably longer amino acid chains. The term "protein" is intended to also encompass derivatized molecules such as glycoproteins and lipoproteins as well as lower molecular weight polypeptides.

As used herein, the term "ubiquitinated polypeptide" refers to a polypeptide bound to ubiquitin, a ubiquitin-like protein (e.g., NEDD8 or ISG15) or a portion thereof. Preferably, ubiquitination is the formation an isopeptide bond between the C-terminal glycine of ubiquitin (or ubiquitin-like protein see e.g., J Proteome Res. 2008 March; 7(3): 1274-87) and the 8-amino group of a lysine present in the target. (See e.g., FIG. 1).

As used herein, a "ubiquitin remnant" or a "ubiquitin tag" is that portion of a ubiquitinated polypeptide which remains attached to the digestion product of the ubiquitinated polypeptide which has been exposed to a hydrolyzing agent such as trypsin. Preferably, the ubiquitin remnant is a diglycine modified epsilon amine of lysine, which adds about 114 daltons to the mass of the lysine residue (see FIG. 1). It is also referred to herein as "K(GG)." Trypsin digestion of neddylated proteins leaves the same K(GG) remnant as trypsin digestion of protein that is attached to ubiquitin.

A "ubiquitin remnant peptide" is the product that results from the digestion of a ubiquitinated polypeptide with a hydrolyzing agent such as trypsin, i.e., a peptide containing at least one ubiquitin remnant. In the preferred embodiment of the invention, a binding partner is used that specifically recognizes and binds to a ubiquitin remnant peptide but does not cross react with other peptides having the same amino acid sequence but which lack the ubiquitin remnant. The preferred binding partner is an antiubiquitin remnant peptide antibody or fragment thereof.

The term "variant" as used herein relative to ubiquitin remnant peptides, refers to a peptide having a ubiquitin remnant that possesses a similar or identical amino acid sequence as a ubiquitin remnant peptide (e.g., one disclosed in Table 4). A variant having a similar amino acid sequence refers to a peptide comprising, or alternatively consisting of, an amino acid sequence that is at least 60%, at least 65%, at least 70%, at least 75%, at least 80%, at least 85%, at least 90%, at least 95%, at least 96%, at least 97%, at least 98% or at least 99% identical to the predicate ubiquitin remnant peptide. Peptide variants also include those having a deletion, substitution and/or addition of about 1 to about 2; about 1 to about 3; or about 1 to about 4 amino acids relative to the predicate ubiquitin remnant peptide.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity number of identical overlapping positions/total number of positions×100%). In one embodiment, the two sequences are the same length.

The term "fragment" as used herein refers to a peptide comprising a ubiquitin remnant and an amino acid sequence of at least 3 amino acid residues, at least 5 amino acid residues, at least 7 amino acid residues, at least 10 amino acid residues, at least 15 amino acid residues, at least 20 amino acid residues, at least 25 amino acid residues, at least 30 amino acid residues of a ubiquitin remnant peptide.

As used herein, the term "biological sample" refers to a readily obtainable mixture of a plurality of polypeptides present in varying concentrations. Preferred biological samples have about 5,000 to about 20,000 different polypeptides. More preferably, biological samples have about 7,500 to about 15,000 different polypeptides. Most preferably, biological samples have about 10,000 different polypeptides. Generally, such samples are environmental, industrial, veterinary or medical in origin and from an animal, plant, a bacterium, a fungus, a protist or a virus. The preferred biological samples include but are not limited to saliva, mucous, tears, blood, serum, lymph/interstitial fluids, buccal cells, mucosal cells, cerebrospinal fluid, semen, feces, plasma, urine, a suspension of cells, or a suspension of cells and viruses. The most preferred biological samples are mammalian, more preferably human, serum and urine.

Where the biological sample is blood, serum or lymph/interstitial fluid, the invention envisages an optional step of depleting the biological sample of common and disproportionally over-represented background proteins not suspected of being associated with ubiquitinated polypeptides. Such proteins include but are not limited to albumin, IgG, IgA, transferrin, haptoglobin, and anti-trypsin; or combinations thereof. The skilled artisan will recognized that such a step is carried out by basic affinity chromatography techniques. As used here in the term "depleted" or "depleting" means markedly lessening the concentration of a particular species in a solution, e.g., by more than or about 50%; more than or about 60%; more than or about 65%; more than or about 70%; more than or about 75%; more than or about 80%; more than or about 85%; more than or about 90%; more than or about 92%; more than or about 95%; more than or about 97%; more than or about 98%; more than or about 99%. Alternatively the biological sample may be a subcellular fraction of a cell line or tissue, enriched for specific cellular organelles such as nuclei, cytoplasm, plasma membranes, mitochondria, internal membrane structures, Golgi apparatus, endoplasmic reticulum, etc. or specific tissue organelles such as post-synaptic densities from brain, islets from pancreas, etc.

As used herein, the term "hydrolyzing agent" refers to any one or combination of a large number of different enzymes, including but not limited to trypsin, Lysine-C endopeptidase (LysC), arginine-C endopeptidase (ArgC), Asp-N, glutamic acid endopeptidase (GluC) and chymotrypsin, V8 protease and the like, as well as chemicals, such as cyanogen bromide. In the subject invention one or a combination of hydrolyzing agents cleave peptide bonds in a protein or polypeptide, in a sequence-specific manner, generating a predictable collection of shorter peptides (a "digest"). A portion of the biological samples are contacted with hydrolyzing agent(s) to form a digest of the biological sample. Given that the amino acid sequences of certain polypeptides and proteins in biological samples are often known and that the hydrolyzing agent(s) cuts in a sequence-specific manner, the shorter peptides in the digest are generally of a predicable amino acid sequence. Preferably, the treatment of a polypeptide with a hydrolyzing agents results in about 2 to about 20, more preferably about 5 to about 15 and most preferably about 10 peptides. If the polypeptide in a biological sample is a ubiquitinated polypeptide, at least one of the resulting peptides in the digest will be a ubiquitin remnant peptide. The preferred hydrolyzing agent is a protease, or chemical which cleaves ubiquitinated proteins in a manner that results in the formation of at least one ubiquitin remnant peptide. Most preferably, the protease is trypsin.

The term "mass spectrometer" means a device capable of detecting specific molecular species and measuring their accurate masses. The term is meant to include any molecular detector into which a polypeptide or peptide may be eluted for detection and/or characterization. In the preferred MS procedure, a sample, e.g., the elution solution, is loaded onto the MS instrument, and undergoes vaporization. The components of the sample are ionized by one of a variety of methods (e.g., by electrospray ionization or "ESI"), which results in the formation of positively charged particles (ions). The positive ions are then accelerated by a magnetic field. The computation of the mass-to-charge ratio of the particles is based on the details of motion of the ions as they transit through electromagnetic fields, and detection of the ions. The preferred mass measurement error of a mass spectrometer of the invention is 10 ppm or less, more preferable is 7 ppm or less; and most preferably 5 ppm or less.

Fragment ions in the MS/MS and MS3 spectra are generally highly specific and diagnostic for peptides of interest. In contrast, to prior art methods, the identification of peptide diagnostic signatures provides for a way to perform highly selective analysis of a complex protein mixture, such as a cellular lysate in which there may be greater than about 100, about 1000, about 10,000, or even about 100,000 different kinds of proteins. Thus, while conventional mass spectroscopy would not be able to distinguish between peptides with different sequences but similar m/z ratios (which would tend to co-elute with any labeled standard being analyzed), the use of peptide fragmentation methods and multistage mass spectrometry in conjunction with LC methods, provide a way to detect and quantify target proteins which are only a small fraction of a complex mixture (e.g., present in less than 2000 copies per cell or less than about 0.001% of total cellular protein) through these diagnostic signatures.

Test peptides are preferably examined by monitoring of a selected reaction in the mass spectrometer. This involves using the prior knowledge gained by the characterization of a standard peptide and then requiring the mass spectrometer to continuously monitor a specific ion in the MS/MS or MS spectrum for both the peptide of interest and the standard peptide. After elution, the areas-under-the-curve (AUC) for both the standard peptide and target peptide peaks may be calculated. The ratio of the two areas provides the absolute quantification that may then be normalized for the number of cells used in the analysis and the protein's molecular weight, to provide the precise number of copies of the protein per cell.

As used herein the term, "accurate mass" refers to an experimentally or theoretically determined mass of an ion that is used to determine an elemental formula. For ions containing combinations of the elements C, H, N, O, P, S, and the halogens, with mass less than 200 Unified Atomic Mass Units, a measurement about 5 ppm uncertainty is sufficient to uniquely determine the elemental composition.

As used herein the term, "predetermined peptide accurate mass" refers to the experimentally determined or calculated accurate mass of a peptide with a known amino acid sequence (along with any associated post-translational modifications). The accurate mass of any such specific amino acid sequence may be readily calculated by one of skill in the art.

As used herein, "a peptide fragmentation signature" refers to the distribution of mass-to-charge ratios of fragmented peptide ions obtained from fragmenting a peptide, for example, by collision induced disassociation, ECD, LID, PSD, IRNPD, SID, and other fragmentation methods. A peptide fragmentation signature which is "diagnostic" or a "diagnostic signature" of a target protein or target polypeptide is one which is reproducibly observed when a peptide digestion product of a target protein/polypeptide identical in sequence to the peptide portion of a standard peptide, is fragmented and which differs only from the fragmentation pattern of the standard peptide by the mass of the mass-altering label and/or the presence of a ubiquitin remnant. Preferably, a diagnostic signature is unique to the target protein (i.e., the specificity of the assay is at least about 95%, at least about 99%, and preferably, approaches 100%).

The term "substrate" includes any solid support or phase upon which a binding partner may be immobilized. Preferred supports are those well known in the art of affinity chromatography for example but not limited to polymeric and optionally magnetic beads, polystyrene, sepharose or agarose gel matrices, or nitrocellulose membranes.

The term "binding partner" refers to any of a large number of different molecules or aggregates. Preferably, a binding partner functions by binding to a polypeptide or peptide in order to enrich it prior to analysis, e.g., by MS, LC-MS, or LC-MS/MS. Preferably, binding partners bind ubiquitin remnant peptides to enrich in a digest. Proteins, polypeptides, peptides, nucleic acids (oligonucleotides and polynucleotides), antibodies, ligands, polysaccharides, microorganisms, receptors, antibiotics, and test compounds (particularly those produced by combinatorial chemistry) may each be a binding partner.

In the preferred one embodiment, the binding partner is immobilized by being directly or indirectly, covalently or non-covalently bound to the substrate. In another embodiment, the binding partner does not require a substrate and can be used to immuno-precipitate the ubiquitin remnant peptides for example. In a further embodiment, the binding partner can be used to bind ubiquitin remnant peptides in solution. The technician could then enrich for ubiquitin remnant peptides by filtering ubiquitin remnant peptide-binding partner complexes, through size cut-off or size exclusion chromatography for example.

The preferred binding partner is a "ubiquitin remnant peptide specific antibody" or an "anti-ubiquitin remnant antibody" which specifically yet reversibly binds ubiquitin remnant peptides and does not bind (i.e., cross react with) peptides having the same amino acid sequence but which lack the ubiquitin remnant. As such, the preferred ubiquitin remnant peptide-specific antibodies bind ubiquitin remnant peptides in a context independent manner.

Accordingly, the invention provides an isolated antibody or binding partner that preferentially binds a ubiquitin remnant peptide over a peptide having the same amino acid sequence as the ubiquitin remnant peptide but lacks the ubiquitin remnant. In some embodiments, the isolated antibody or binding partner specifically binds a ubiquitin remnant peptide but does not specifically bind a peptide having the same amino acid sequence as the ubiquitin remnant peptide but lacks the ubiquitin remnant. As used herein, by "specifically binds" is meant that a binding partner or an antibody of the invention interacts with its target molecule (e.g., a ubiquitin remnant peptide), where the interaction is dependent upon the presence of a particular structure (e.g., the antigenic determinant or epitope on the peptide); in other words, the reagent is recognizing and binding to a specific polypeptide structure rather than to all polypeptides in general. In some embodiments, the isolated antibodies or isolated binding partners do not specifically bind to a peptide having the same amino acid sequence as the ubiquitin remnant peptide but lacks the ubiquitin remnant.

The isolated antibodies and/or isolated binding partners of the invention can be used in the methods of the invention.

It should be understood that the substrate can have a number many different binding partners having a different binding specificity for a different polypeptide, peptide, ubiquitin remnant peptide or epitopes thereof. As such, binding partners might be derived from monoclonal sources or polyclonal sera. Preferably, the substrate has about 2 to about 500, more preferably about 5 to about 400, even more preferably about 10 to about 300 and most preferably about 15 to about 200, yet even more preferably about 20 to about 100, about 25 to about 75 and about 30 to about 60 different binding partners each specifically binding to a different and/or distinct peptide. This allows the technician to simultaneously process and analyze the biological sample for the presence of a large number of polypeptides in a manner not feasible with multiplex PCR or ELISA techniques. Additional methods and reagents for immunoaffinity purification and/or enrichment of peptides containing certain motifs such as the ubiquitin remnant may be found in e.g., in U.S. Pat. Nos. 7,198,896 and 7,300,753.

The motif-specific, context-independent antibodies of the invention produced by this method provide the ability to specifically recognize multiple peptides or proteins within a genome that contain the same motif using a single antibody. In a preferred embodiment, the antibodies of the invention recognize a majority of peptides or proteins containing the motif within a genome. For example, the antibodies of the invention may be used to identify an unknown substrate of an enzyme. In a preferred embodiment, such antibodies are first generated against the modified form of a motif that is recognized by the enzyme of interest, for example, a consensus site. These antibodies are then used to screen a sample for the presence of other, unknown substrates which contain the same modified motif. This method enables the rapid detection of important new substrates in a variety of cascades which involve conserved substrate motifs. For example, antibodies that selectively recognize a wide variety of proteins only when phosphorylated at the MAPK consensus phosphorylation site would greatly facilitate the detection of new MAP kinase targets. The highly context-independent antibodies of the invention enable such genome-wide profiling, as they recognize many of, if not most, peptides or proteins containing the same short motif. MAP kinase could be overexpressed in cell culture, activated by growth factors, and target substrate proteins identified by western blotting using antibodies that selectively recognize the phosphorylated substrate proteins (Stukenberg et al., Curr. Biol. 7:338-348 (1997). Alternatively, MAPK could be used to phosphorylate cDNA expression libraries in vitro and MAPK consensus-site antibodies used to identify cDNA clones expressing MAPK phosphorylated substrates (Funkunaga and Hunter, EMBO 16(8):1921-1933 (1997). Similarly, the method may be employed to identify new substrates containing specific unmodified motifs, e.g. protein cleavage motifs.

Similarly, motif-specific, context-independent antibodies of the instant invention may be used to identify an enzyme which modifies a known substrate motif. Such antibodies, whether specific for modified (e.g. phosphorylated) or unmodified (e.g. zinc finger) motifs, can be used to detect whether a certain enzyme of interest has modified a substrate which contains that motif. This method allows for the rapid detection of important new proteins which act on known classes of substrates containing contain conserved motifs, for the example MAPK consensus site. In a preferred embodiment, the antibody recognizes the modified form of the motif, and an enzyme sample is reacted with known substrate containing the unmodified form of the motif, and the antibody then used to screen whether any substrate has been modified by the enzyme. Alternatively, the method may be employed to identify enzymes that act on unmodified motifs, such as protein cleavage motifs.

The motif-specific, context-independent antibodies of the invention may also be used in vitro as reagents in high-throughput assays, such as drug screens, to detect the enzymatic modification of certain substrates containing a conserved motif in a cell or tissue. For example, antibodies specific for a certain phosphorylated motif enable the rapid detection of inhibitors of the enzyme that act at that motif. In the case of a drug screen, a single motif-specific antibody can be used to assay the activity of a wide range of enzymes acting at many diverse sequence motifs. Phosphotyrosine antibodies are currently employed in high throughput kinase assays to screen for selective, high affinity tyrosine kinase inhibitors. Compounds or drugs that block enzyme activity are detected by their ability to inhibit kinase activity as determined by a reduction of phosphotyrosine antibody binding to phosphorylated substrate. Similar assays can be set up to screen for pharmaceutically useful compounds using antibodies produced as described above for phosphoserine, phosphothreonine, or antibodies detecting other protein modifications. In a preferred embodiment, the antibody recognizes the modified form of a common motif, and is used to screen an extract of a cell or tissue treated with a drug to profile drug-induced changes in the level or post-translational modification of proteins in the extract that contain the modified motif.

Antibody based detection of protein kinase activity has several advantages over radioactive assays for use in automated high throughput kinase assays. First, radioactive assays are difficult to automate because they employ transfer of 32-P gamma-labeled ATP to a peptide substrate. The phosphopeptide is then separated from labeled ATP using phosphocellulose filters and several washing steps, and finally, phosphorylation is quantitated by liquid scintillation methods. Together these steps are time consuming and difficult to automate. Antibody detection allows a wide variety of ELISA-type assays that are well suited for automation and high throughput screens.

Second, radioactive assays require low levels of ATP to insure high levels of 32-P incorporation for maximal sensitivity. Low levels of ATP in the kinase assay bias the search for inhibitors towards compounds that compete with ATP binding in the protein kinase catalytic cleft. Such screens consistently yield competitive inhibitors at the ATP binding site which due to the highly conserved nature of this binding site results in inhibitors with poor selectivity.

Current high-throughput kinase assays typically utilize biotinylated peptide substrates immobilized on the bottom of a 96 or 386 well plate that is subsequently incubated together with the desired protein kinase, ATP, and the appropriate kinase buffer. Kinase activity is measured using a fluorescently labeled phosphospecific-antibody that reacts only with the phosphorylated peptide substrate. These assays come in two formats homogeneous (not involving wash steps and heterogeneous (involving wash steps). Homogeneous fluorescent assays typically utilize lanthanide-labeled phosphoantibody binding to a phosphorylated peptide substrate that has linked to it an energy acceptor, for example allophycocyanin. Binding of the phosphoantibody the phosphorylated peptide substrate brings the two fluorophores close enough together to allow fluorescence resonance energy transfer to occur shifting the frequency of the emitted signal, indicating the presence of a biomolecular complex. Different compounds are added to each well and the ability of the compound to inhibit substrate phosphorylation is determined by inhibition of fluorescence energy transfer. This format is similar to the scintillation proximity assay commonly used in radioactive assays. Other homogeneous assays involve the use of fluorescence polarization to measure the binding of phosphoantibody to phosphorylated substrate.

The key feature in the homogeneous assays are the limited number of steps and the ease in automation. A large variety of heterogeneous kinase assays based upon ELISA formats are also currently in use. These assays typically utilizing fluorescently labeled phosphoantibodies binding phosphorylated peptide substrates that are immobilized in 96 or 386 well formats. In this case wash steps are required to separate bound from unbound antibody. Fluorescently labeled antibody retained in the well is then detected using time resolved fluorescence.

The motifs used to generate antibodies for such modification screening assays may be either modified or unmodified substrate motifs. Antibodies generated against unmodified motifs will not bind if the substrate has been subsequently modified by an enzyme. Similarly, antibodies generated against modified motifs can detect increases in modified substrate concentrations owing to enzymatic activity.

Similar approaches may be applied to study a variety of other enzymatic modifications, and are not limited to the protein kinase or acetyltransferase activities discussed below. For example, the approach could be used to generate antibodies that recognize many other types of protein modification, including, but not limited to, the addition of sugars, methyl groups, carboxyl groups, the addition of various lipids, or the addition of nucleotides, or polymers of nucleotides, nucleosides, or amino acids such as ubiquitin.

Likewise, such motif-specific, context-independent antibodies may be used on a genome-wide scale to simultaneously profile large and diverse protein populations (e.g. in a cell, tissue, or fluid) which contain conserved motifs. A specific two or three amino acid binding site, for example consecutive arginine residues, should appear (based upon a random distribution of amino acids) once every 400 or 8000 residues, respectively, (equating to approximately once per protein, or once every 20 proteins, respectively, (assuming the average protein is 400 amino acids)). Thus, an antibody that specifically recognizes such a motif in a manner that is substantially independent of the context in which it occurs allows for the rapid screening of a great number of proteins or peptides containing the motif. For example, there at least 14 known human proteins containing the AKT consensus substrate motif. See Yaffe et al., supra at p. 350 (Table 1). A context-independent antibody specific for all or part of this motif thus allows for the single-antibody detection of these many motif-containing AKT substrates, as well as the identification of other unknown AKT substrates containing the same consensus motif.

The term "antibody" as used herein, refers to immunoglobulin molecules and immunologically active portions of immunoglobulin molecules, i.e., molecules that contain an antigen binding site that specifically binds to an antigen. As such, the term antibody encompasses not only whole antibody molecules, but also antibody multimers and antibody fragments, as well as variants (including derivatives) of antibodies, antibody multimers and antibody fragments.

The basic antibody structural unit is known to comprise a tetramer. Each tetramer is composed of two identical pairs of polypeptide chains, each pair having one "light" (about 25 kilodalton) and one "heavy" chain (about 50-70 kilodalton). The amino-terminal portion of each chain includes a variable region of about, 80, 85, 90, 95, 100, 105, preferably 100 to 110 or more amino acids primarily responsible for antigen recognition. Herein the terms "heavy chain" and "light chain" refer to the heavy and light chains of an antibody unless otherwise specified. The amino acid sequence of the D4A7A10 heavy chain is set forth in SEQ ID NO: 1. The amino acid sequence of the D4A7A10 light chain is set forth in SEQ ID NO: 2.

The carboxy-terminal portion of each chain preferably defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, Fundamental Immunology Ch. 7 (Paul, W., ed., 2nd ed. Raven Press, N.Y. (1989)) (incorporated by reference in its entirety for all purposes). The variable regions of each light ("VL")/heavy chain ("VH") pair preferably form the antibody binding site. Thus, an intact IgG antibody has two binding sites. Except in bifunctional or bispecific antibodies, the two binding sites are the same. The chains all exhibit the same general structure of relatively conserved framework regions (FR) joined by three hyper variable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, J. Mol. Biol. 196: 901-917 (1987); Chothia et al., Nature 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann Clin. Exp. Immunol. 79: 315-321 (1990), Kostelny et al. J. Immunol. 148:1547 1553 (1992). In addition, bispecific antibodies may be formed as "diabodies" (Holliger et al. "'Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" EMBO J. 10:3655-3659 (1991) and Traunecker et al. "Janusin: new molecular design for bispecific reagents" Int J Cancer Suppl 7:51-52 (1992)). Production of bispecific antibodies can be a relatively labor intensive process compared with production of conventional antibodies and yields and degree of purity are generally lower for bispecific antibodies.

Examples of molecules which are described by the term "antibody" herein include, but are not limited to: single chain Fvs (sdFvs), Fab fragments, Fab' fragments, F(ab')2, disulfide linked Fvs (sdFvs), Fvs, and fragments thereof comprising or alternatively consisting of, either a VL or a VH domain. The term "single chain Fv" or "scFv" as used herein refers to a polypeptide comprising a VL domain of antibody linked to a VH domain of an antibody.

Antibodies of the invention include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Preferably, an antibody of the invention comprises, or alternatively consists of, a VH domain, VH CDR, VL domain, or VL CDR having an amino acid sequence of any one of the antibodies listed in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms. Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')2 fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1 carboxylate] and SATA [Nsuccinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, The Journal of Immunology (2002) 25:396-404, which is hereby incorporated by reference in its entirety.

Alternatively, antibodies can be made to multimerize through recombinant DNA techniques. IgM and IgA naturally form antibody multimers through the interaction with the mature J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31. and Frigerio et al., (2000) Plant Physiology 123:1483-94, both of which are hereby incorporated by reference in their entireties.) IgA dimers are naturally secreted into the lumen of mucosa-lined organs. This secretion is mediated through interaction of the J chain with the polymeric IgA receptor (pIgR) on epithelial cells. If secretion of an IgA form of an antibody (or of an antibody engineered to contain a J chain interaction domain) is not desired, it can be greatly reduced by expressing the antibody molecule in association with a mutant J chain that does not interact well with pIgR (Johansen et al., The Journal of Immunology (2001) 167:5185-5192 which is hereby incorporated by reference in its entirety). ScFv dimers can also be formed through recombinant techniques known in the art; an example of the construction of scFv dimers is given in Goel et al., (2000) Cancer Research 60:6964-6971 which is hereby incorporated by reference in its entirety. Antibody multimers may be purified using any suitable method known in the art, including, but not limited to, size exclusion chromatography.

Monoclonal and polyclonal context-independent ubiquitin remnant peptide antibodies have been identified. For example, the invention encompasses the monoclonal and polyclonal antibodies listed in Table 1 and the cell lines engineered to express them or capable of expressing them.

Further, the present invention encompasses the polynucleotides encoding the anti-ubiquitin remnant peptide antibodies or portions thereof. Molecules encoding e.g., VH domains, VH CDRs, VL domains, or VL CDRs having an amino acid sequence of the corresponding region of the inventive antibodies expressed by a cell that specifically bind to ubiquitin remnant peptides but not peptides having the same amino acid sequence but lacking the ubiquitin remnant, or fragments or variants thereof are also encompassed by the invention, as are nucleic acid molecules that encode these antibodies and/or molecules. In specific embodiments, the present invention encompasses antibodies, or fragments or variants thereof that bind to an epitope that comprises the ubiquitin remnant.

Methods for identifying the complementarity determining regions (CDRs) of an antibody by analyzing the amino acid sequence of the antibody are well known (see, e.g., Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol. Biol. 275(2):269-94 (January 1998); Chothia et al., Nature 342(6252):877-83 (December 1989); Ponomarenko and Bourne, BMC Structural Biology 7:64 (2007).

The inventive anti-ubiquitin remnant peptide antibodies may be coupled to a detectable label such as an enzyme, a fluorescent label, a luminescent label, or a bioluminescent label.

The present invention also provides anti-ubiquitin remnant peptide antibodies that are coupled to a therapeutic or cytotoxic agent. The present invention also provides anti-PA antibodies which are coupled, directly or indirectly, to a radioactive material.

In further embodiments, the anti-ubiquitin remnant peptide antibodies of the invention have a dissociation constant ($K_D$) of $10^{-7}$ M or less for a ubiquitin remnant peptide. In preferred embodiments, the anti-ubiquitin remnant peptide antibodies of the invention have a dissociation constant ($K_D$) of $10^{-9}$ M or less for a ubiquitin remnant peptide.

In further embodiments, antibodies of the invention have an off rate ($k_{off}$) of $10^{-3}$ sec$^{-1}$ or less. In preferred embodiments, antibodies of the invention have an off rate ($k_{off}$) of $10^{-4}$ sec$^{-1}$ or less. In other preferred embodiments, antibodies of the invention have an off rate ($k_{off}$) of $10^{-5}$ sec$^{-1}$ or less.

The present invention also provides panels of the anti-ubiquitin remnant peptide antibodies (including molecules comprising, or alternatively consisting of, antibody fragments or variants) wherein the panel members correspond to one, two, three, four, five, ten, fifteen, twenty, or more different the anti-ubiquitin remnant peptide antibodies of the invention (e.g., whole antibodies, Fabs, F(ab')2 fragments, Fd fragments, disulfide-linked Fvs (sdFvs), anti-idiotypic (anti-Id) antibodies, and scFvs). The present invention further provides mixtures of the anti-ubiquitin remnant peptide antibodies wherein the mixture corresponds to one, two, three, four, five, ten, fifteen, twenty, or more different the anti-ubiquitin remnant peptide antibodies of the invention (e.g., whole antibodies, Fabs, F(ab')2 fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more the anti-ubiquitin remnant peptide antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more of the anti-ubiquitin remnant peptide antibodies or fragments or variants thereof. Alternatively, a composition of the invention may comprise, or alternatively consist of, nucleic acid molecules encoding one or more antibodies of the invention.

The present invention also provides for fusion proteins comprising an anti-ubiquitin remnant peptide antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention.

Alternatively, a composition of the invention may comprise, or alternatively consist of, nucleic acid molecules encoding one, two, three, four, five, ten, fifteen, twenty or more fusion proteins of the invention.

The term "elution solution" refers to a solution that when brought into contact with the binding partner, results in the dissociation of the polypeptide or peptide and preferably the ubiquitin remnant peptide from the binding partner into the elution solution. Determining the salt, pH and ionic conditions necessary for such functionality is well with the ordinary skill in the art. Preferably, the elution solution is enriched for polypeptides and peptides which were bound to the binding partners relative to the polypeptides and peptides of the digest. Preferably, the elution solution has about 500 to about 5000, more preferably about 1000 to about 2000 different peptides. Most preferably, the elution solution is enriched for ubiquitin remnant peptides. Preferably, a portion of the elution solution is directly transferred to a mass spectrometer, LC-MS or LC-MS/MS. Alternatively, the elution solution is subject to further manipulation e.g., to concentrate the peptides and/or polypeptides contained therein. Mechanisms for directing solutions from liquid chromatography to mass spectrometers may be found for example in U.S. Pub. No. 20080217254.

The term "vaporizing a portion of the elution solution" means that a portion of the elution solution is preferably transferred to a mass spectrometer for vaporization and ionization.

The term "ionizing" refers to atmospheric pressure chemical ionization (APCI), chemical ionization (CI), electron impact (O), electrospray ionization (ESI), fast atom bombardment (FAB), field desorption/field ionization (FD/FI), matrix assisted laser desorption ionization (MALDI), and thermospray ionization. The preferred method of ionization is ESI as tends to minimize the propensity of macromolecules to fragment when ionized.

Preferably in ESI, liquid containing the peptides of interest is dispersed by electrospray into a fine aerosol. Preferred solvents for electrospray ionization are prepared by mixing water with volatile organic compounds (e.g. methanol, acetonitrile). To decrease the initial droplet size, compounds that increase the conductivity (e.g. acetic acid) are preferably added to the solution. Large-flow electrosprays may provide additional nebulization by an inert gas such as nitrogen. The aerosol is sampled into the first vacuum stage of a mass spectrometer through a capillary, which can be heated to aid further solvent evaporation from the charged droplets. Preferably, the solvent evaporates from a charged droplet until it becomes unstable upon reaching its Rayleigh limit. At this point, the droplet preferably deforms and emits charged jets in a process known as Rayleigh fission. During the fission, the droplet loses a small percentage of its mass along with a relatively large percentage of its charge As used herein, "ionized molecule" refers to molecules in the elution solution that have become charged and are ready to move into the electric fields that will direct them into the mass analyzer of a mass spectrometer. Preferably, the ionized molecules include ionized polypeptides, peptides and/or ubiquitin remnant peptides present in the elution solution. Most preferably, the ionized molecules are ubiquitin remnant peptides.

The term "standard peptide" as used herein, refers to a peptide that is 1) recognized as equivalent to a peptide of interest in the digest generated by a hydrolyzing agent, e.g., the ubiquitin remnant peptide, by the appropriate binding partner; and 2) differs from the peptide of interest in a manner that can be distinguished by a mass spectrometer, e.g., by way of a mass-altering label. Preferably, the standard peptide has the same amino acid sequence as the ubiquitin remnant peptide but is synthesized utilizing elemental isotopes. Preferably, those isotopes are N-15, C-13, O-18 or H-2. Alternatively, a standard peptide can 1) have the same amino acid sequence as a ubiquitin remnant peptide yet lack the ubiquitin remnant; and 2) differ from the ubiquitin remnant peptide in a manner that can be distinguished by a mass spectrometer, e.g., by lacking the ubiquitin remnant. Exemplary standard peptides are described in U.S. Pub. No. 20060154318 and 20060148093. One or more standard peptides may be added to the biological sample before or after treatment with a hydrolyzing agent such that it co-elutes with the peptide of interest into the elution solution. The standard peptide can be added directly to the elution solution.

One aspect of the invention relates to providing methods for determining a site of ubiquitination in a polypeptide. The method comprises obtaining a plurality of ubiquitinated polypeptides; digesting the ubiquitinated polypeptides with a protease, thereby generating a plurality of test peptides; enriching the plurality of test peptides for ubiquitin remnant peptides; and determining the presence of a ubiquitin remnant peptide by mass spectrometry, wherein the presence of the ubiquitin remnant peptide allows the technician to determine a site of ubiquitination of the polypeptide. The test peptide being evaluated can be ionized and/or fragmented prior to the determining step. Preferably, ionizing is performed by electrospray.

In one embodiment of this aspect of the invention, the method for determining a site of ubiquitination comprises obtaining a plurality of ubiquitinated polypeptides; digesting the ubiquitinated polypeptides with a protease; thereby generating a plurality of test peptides; at least some of which comprise a ubiquitin remnant, enriching the plurality of test peptides for ubiquitin remnant peptides; and identifying a mass difference between a test peptide and a standard peptide comprising a known identical amino acid sequence as the test peptide; the mass difference corresponding to the mass of the ubiquitin remnant, wherein detection of the mass difference indicates a site of ubiquitination in the test peptide.

In another aspect, the methods further comprise the step of mapping a sequence of a test peptide comprising a ubiquitin remnant to a polypeptide sequence comprising the same amino acid sequence as the test peptide, thereby determining the site of ubiquitination in the polypeptide sequence. In another embodiment, the ubiquitin remnant comprises GlyGly amino acid residues and has a mass of about 114 daltons. The methods can be used to detect one or more sites of ubiquitination in a polypeptide, as well as the amount of ubiquitination at particular sites in a population of polypeptides.

In a further aspect of the invention, ubiquitination sites are identified for a plurality of polypeptides in a first cell and in a second cell and the sites identified in the first cell are compared to those in the second cell. In one aspect, the first cell is a normal cell (e.g., from a healthy patient), while the second cell is from a patient with a pathological condition (e.g., a neurodegenerative disease, cancer, a disease of the immune system). Preferably, the second cell is the target of the pathology (e.g., a tumor cell from a cancer patient; a neural cell from a patient with a neurodegenerative disease). In another embodiment of this aspect of the invention, the second cell differs from the first cell in expressing one or more recombinant DNA molecules, but is otherwise genetically identical to the first cell. In a further embodiment, the site of ubiquitination is correlated with disease and detection of ubiquitination at the site is associated with risk of the disease. In another embodiment, the disease is a neurodegenerative disease, such as Alzheimer's or Pick's disease. In another aspect, the disease is cancer. In a further aspect, the disease is an abnormal immune response or inflammatory disease.

In another aspect of the invention, the methods disclosed herein are used to identify regulators of ubiquitination pathways. In one embodiment, the methods further comprise contacting a first cell with a compound and comparing ubiquitination sites identified in the first cell with ubiquitination sites in a second cell not contacted with the compound. The compound may be a therapeutic agent for treating a disease associated with an improper state of ubiquitination (e.g., abnormal sites or amounts of ubiquitination). Suitable agents include, but are not limited to, drugs, polypeptides, peptides, antibodies, nucleic acids (genes, cDNAs, RNA's, antisense molecules, siRNA/miRNA constructs, ribozymes, aptamers and the like), toxins, and combinations thereof.

Preferably, the methods further comprise generating a database comprising data files storing information relating to ubiquitination sites for a plurality of polypeptides for a plurality of different cells. Preferably, the data files also include information relating to amount of ubiquitination of a polypeptide in at least one cell. Additionally, the database comprises data relating to the source of the cell (e.g., such as a patient).

The invention further provides a computer memory comprising data files storing information relating to ubiquitination sites for a plurality of polypeptides for a plurality of different cells.

In another aspect of the invention, substantially purified test peptides, preferably ubiquitin remnant peptides, obtained after one or more separation steps are analyzed by a peptide analyzer that evaluates the mass of the peptide or a fragment thereof. Suitable peptide analyzers include, but are not limited to, a mass spectrometer, mass spectrograph, single-focusing mass spectrometer, static field mass spectrometer, dynamic field mass spectrometer, electrostatic analyzer, magnetic analyzer, quadropole analyzer, time of flight analyzer (e.g., a MALDI Quadropole time-of-flight mass spectrometer), Wien analyzer, mass resonant analyzer, double-focusing analyzer, ion cyclotron resonance analyzer, ion trap analyzer, tandem mass spectrometer, liquid secondary ionization MS, and combinations thereof in any order (e.g., as in a multi-analyzer system). Such analyzers are known in the art and are described in, for example, Mass Spectrometry for the Biological Sciences, Burlingame and Can eds., Human Press, Totowa, N.J.)

In general, any analyzer can be used that can separate matter according to its anatomic and molecular mass. Preferably, the peptide analyzer is a tandem MS system (an MS/MS system) since the speed of an MS/MS system enables rapid analysis of low femtomole levels of peptide and can be used to maximize throughput.

In a preferred embodiment of this aspect of the invention, the peptide analyzer comprises an ionizing source for generating ions of a test peptide and a detector for detecting the ions generated. The peptide analyzer further comprises a data system for analyzing mass data relating to the ions generated and for deriving mass data relating to the test peptide.

A sample comprising a test peptide can be delivered to the peptide analyzer using a delivery mechanism as described above. Interfaces between a sample source (e.g., an HPLC column) and ion source can be direct or indirect. For example, there may be an interface that provides for continuous introduction of the sample to the ion source. Alternatively, sample can be intermittently introduced to the ion source (e.g., in response to feedback from the system processor during the separation process, or while the separation system is off-line).

In another embodiment, the ion source is an electrospray which is used to provide droplets to the peptide analyzer, each droplet comprising a substantially purified test peptide obtained from previous separation step(s) (e.g., such as HPLC or reversed phase liquid chromatography). During electrospray, a high voltage is applied to a liquid stream causing large droplets to be subdivided into smaller and smaller droplets until a peptide enters the gas phase as an ion. Ionization generally is accomplished when the test peptide loses or gains a proton at one or more sites on the peptide (e.g., at the amino terminus, and/or at lysine and arginine residues). Ionization in electrospray is constant; MALDI can be used to achieve pulsed ionization. Other methods of ionization, include but are not limited to, plasma desorption ionization, thermospray ionization, and fast atom bombardment ionization as are known in the art.

When MALDI is used, peptides can be delivered to a solid support, e.g., sample plate inserted into the mass spectrometer. The support may comprise a light-absorbent matrix. In another embodiment, a substantially purified ubiquitinated polypeptide is provided on a sample plate and protease digestion occurs on the sample plate prior to ionization. For example, substantially purified ubiquitinated peptides also can be obtained from protease digests as described above and separated by a liquid chromatography method. Preferably, the peptide analyzer further comprises an ion transfer section through which ions are delivered from the ion source to the detector. The ion transfer section comprises an electric and/or magnetic field generator (e.g., an electrode ring) that modulates the acceleration of ions generated by the ionizing source. The electric/magnetic field generator directs ions through the ion transfer section of the peptide analyzer to the ion detector.

Preferably, the peptide analyzer further comprises an ion trap positioned between the ion transfer section of the analyzer and the detector, for performing one or more operations such as ion storage, ion selection and ion collision. The ion trap can be used to fragment ions produced by the ion source (e.g., causing ions to undergo collisional activated dissociation in the presence of a neutral gas ions, such as helium ions). The ion trap also can be used to store ions in stable orbits and to sequentially eject ions based on their mass-to-charge values (m/z) to the detector. An additional separation section can be provided between the ion trap and detector to separate fragments generated in the ion trap (e.g., as in tandem MS). The detector detects the signal strength of each ion (e.g., intensity), which is a reflection of the amount of protonation of the ion.

The peptide analyzer additionally preferably is associated with data system for recording and processing information collected by the detector. The data system can respond to instructions from a processor in communication with the separation system and also can provide data to the processor. Preferably, the data system includes one or more of a computer; an analog to digital conversion module; and control devices for data acquisition, recording, storage and manipulation. More preferably, the device further comprises a mechanism for data reduction, i.e., a device to transform the initial digital or analog representation of output from the analyzer into a form that is suitable for interpretation, such as a graphical display, a table of masses, a report of abundances of ions, etc.)

The data system can perform various operations such as signal conditioning (e.g., providing instructions to the peptide analyzer to vary voltage, current, and other operating parameters of the peptide analyzer), signal processing, and the like. Data acquisition can be obtained in real time, e.g., at the same time mass data is being generated. However, data acquisition also can be performed after an experiment, e.g., when the mass spectrometer is off line.

The data system can be used to derive a spectrum graph in which relative intensity (i.e., reflecting the amount of protonation of the ion) is plotted against the mass to charge ratio (m/z ratio) of the ion or ion fragment. An average of peaks in a spectrum can be used to obtain the mass of the ion (e.g., peptide) (see, e.g., McLafferty and Turecek, 1993, Interpretation of Mass Spectra, University Science Books, CA).

Mass spectra can be searched against a database of reference peptides of known mass and sequence to identify a reference peptide which matches a test peptide (e.g., comprises a mass which is smaller by the amount of mass attributable to a ubiquitin remnant). The database of standard peptides can be generated experimentally, e.g., digesting non-ubiquitinated peptides and analyzing these in the peptide analyzer. The database also can be generated after a virtual digestion process, in which the predicted mass of peptides is generated using a suite of programs such as PROWL (e.g., available from ProteoMetrics, LLC, New York; N.Y.). A number of database search programs exist which can be used to correlate mass spectra of test peptides with amino acid sequences from polypeptide and nucleotide databases, including, but not limited to: the SEQUEST program (Eng, et al., J. Am. Soc. Mass Spectrum. 5: 976-89; U.S. Pat. No. 5,538,897; Yates, Jr., III, et al., 1996, J. Anal. Chem. 68(17): 534-540A), available from Finnegan Corp., San Jose, Calif.

Data obtained from fragmented peptides can be mapped to a larger peptide or polypeptide sequence by comparing overlapping fragments. Preferably, a Ubiquitinated peptide is mapped to the larger polypeptide from which it is derived to identify the ubiquitination site on the polypeptide. Sequence data relating to the larger polypeptide can be obtained from databases known in the art, such as the nonredundant protein database compiled at the Frederick Biomedical Supercomputing Center at Frederick, Md.

In another aspect of the invention, the amount and location of ubiquitination is compared to the presence, absence and/or quantity of other types of polypeptide modifications. For example, the presence, absence, and/or quantity of phosphorylation, sulfation, glycosylation, and/or acetylation can be determined using methods routine in the art (see, e.g., Rossomando, et al., 1992, Proc. Natl. Acad. Sci. USA 89: 5779-578; Knight et al., 1993, Biochemistry 32: 2031-2035; U.S. Pat. No. 6,271,037). The amount and locations of one or more modifications can be correlated with the amount and locations of ubiquitination sites. Preferably, such a determination is made for multiple cell states.

Knowledge of ubiquitination sites can be used to identify compounds that modulate particular ubiquitinated polypeptides (either preventing or enhancing ubiquitination, as appropriate, to normalize the ubiquitination state of the polypeptide). Thus, in one aspect, the method described above may further comprise contacting a first cell with a compound and comparing ubiquitination sites/amounts identified in the first cell with ubiquitination sites/amounts in a second cell not contacted with the compound. Suitable cells that may be tested include, but are not limited to: neurons, cancer cells, immune cells (e.g., T cells), stem cells (embryonic and adult), undifferentiated cells, pluripotent cells, and the like. In one preferred aspect, patterns of ubiquitination are observed in cultured cells, such as P 19 cells, pluripotent embryonic carcinoma cells capable of differentiating into cardiac cells and skeletal myocytes upon exposure to DMSO (see Montross, et al., J. Cell Sci. 113 (Pt. 10): 1759-70).

Compounds which can be evaluated include, but are not limited to: drugs; toxins; proteins; polypeptides; peptides; amino acids; antigens; cells, cell nuclei, organelles, portions of cell membranes; viruses; receptors; modulators of receptors (e.g., agonists, antagonists, and the like); enzymes; enzyme modulators (e.g., such as inhibitors, cofactors, and the like); enzyme substrates; hormones; nucleic acids (e.g., such as oligonucleotides; polynucleotides; genes, cDNAs; RNA; antisense molecules, ribozymes, aptamers); and combinations thereof. Compounds also can be obtained from synthetic libraries from drug companies and other commercially available sources known in the art (e.g., including, but not limited to the LEADQUEST library) or can be generated through combinatorial synthesis using methods well known in the art. A compound is identified as a modulating agent if it alters the site of ubiquitination of a polypeptide and/or if it alters the amount of ubiquitination by an amount that is significantly different from the amount observed in a control cell (e.g., not treated with compound).

In further aspect of the invention, the ubiquitination states (e.g., sites and amount of ubiquitination) of first and second cells are evaluated. Preferably, the second cell differs from the first cell in expressing one or more recombinant DNA molecules, but is otherwise genetically identical to the first cell. Alternatively, or additionally, the second cell can comprise mutations or variant allelic forms of one or more genes. In one aspect, DNA molecules encoding regulators of the ubiquitin pathway can be introduced into the second cell (e.g., E1, E2, E3, deubiquitinating proteins, fragments thereof, mutant forms thereof, variants, and modified forms thereof, or compounds identified as above) and alterations in the ubiquitination state in the second cell can be determined. DNA molecules can be introduced into the cell using methods routine in the art, including, but not limited to: transfection, transformation, electroporation, electro fusion, microinjection, and germline transfer.

The invention also provides methods for generating a database comprising data files for storing information relating to diagnostic peptide fragmentation signatures. Preferably, data in the data files include one or more peptide fragmentation signatures characteristic or diagnostic of a cell state (e.g., such as a state which is characteristic of a disease, a normal physiological response, a developmental process, exposure to a therapeutic agent, exposure to a toxic agent or a potentially toxic agent, and/or exposure to a condition). Data in the data files also preferably includes values corresponding to level of proteins corresponding to the peptide fragmentation signatures found in a particular cell state.

In one embodiment, for a cell state determined by the differential expression of at least one protein, a data file corresponding to the cell state will minimally comprise data relating to the mass spectra observed after peptide fragmentation of a standard peptide diagnostic of the protein. Preferably, the data file will include a value corresponding to the level of the protein in a cell having the cell state. For example, a tumor cell state is associated with the overexpression of p53 (see, e.g., Kern, et al., 2001, Int. J. Oncol. 21(2): 243-9). The data file will comprise mass spectral data observed after fragmentation of a standard corresponding to a subsequence of p53. Preferably, the data file also comprises a value relating to the level of p53 in a tumor cell. The value may be expressed as a relative value (e.g., a ratio of the level of p53 in the tumor cell to the level of p53 in a normal cell) or as an absolute value (e.g., expressed in nM or as a % of total cellular proteins).

Preferably, the data files also include information relating to the presence or amount of a modified form of a target a polypeptide in at least one cell and to mass spectral data diagnostic of the modified form (i.e., peak data for a fragmented peptide internal standard which corresponds to the modified form). More preferably, the data files also comprise spectral data diagnostic of the unmodified form as well as data corresponding to the level of the unmodified form.

In one embodiment, data relating to ubiquitination sites and amounts of ubiquitination are stored in a database to create a proteome map of ubiquitinated proteins. Preferably, the database comprises a collection of data files relating to all ubiquitinated polypeptides in a particular cell type. The database preferably further comprises data relating to the origin of the cell, e.g., such as data relating to a patient from whom a cell was obtained. More preferably, the database comprises data relating to cells obtained from a plurality of patients. In one aspect, the database comprises data relating to the ubiquitination of a plurality of different cell types (e.g., cells from patients with a pathology, normal patients, cells at various stages of differentiation, and the like). In another aspect, data relating to ubiquitination patterns in cells obtained from patients with a neurological disease are stored in the database. For example, information relating to ubiquitination in cell samples from patients having any of Alzheimer's disease; amyotrophic lateral sclerosis; dementia; depression; Down's syndrome; Huntington's disease; peripheral neuropathy; multiple sclerosis; neurofibromatosis; Parkinson's disease; and schizophrenia, can be included in the database.

In a further embodiment, data relating to ubiquitination patterns in cells from patients with cancer are stored in the database, including, but not limited to patients with: adenocarcinoma; leukemia; lymphoma; melanoma; myeloma; sarcoma; teratocarcinoma; and, in particular, cancers of the adrenal gland; bladder; bone; bone marrow; brain; breast; cervix; gall bladder; ganglia; gastrointestinal; tract; heart; kidney; liver; lung; muscle; ovary; pancreas; parathyroid; prostate; salivary glands; skin; spleen; testes; thymus; thyroid; and uterus.

Additionally, data of ubiquitination patterns in cells from patients with an immune disorder may be included in the database. Such a disorder can include: acquired immunodeficiency syndrome (AIDS); Addison's disease; adult respiratory distress syndrome; allergies; ankylosing spondylitis; amyloidosis; anemia; asthma; atherosclerosis; autoimmune hemolytic anemia; autoimmune thyroiditis; bronchitis; cholecystitis; contact dermatitis; Crohn's disease; atopic dermatitis; dermatomyositis; diabetes mellitus; emphysema; episodic lymphopenia with lymphocytotoxins; erythroblastosis fetalis; erythema nodosum; atrophic gastritis; glomerulonephritis; Goodpasture's syndrome; gout; Graves' disease; Hashimoto's thyroiditis; hypereosinophilia; irritable bowel syndrome; myasthenia gravis; myocardial or pericardial inflammation; osteoarthritis; osteoporosis; pancreatitis; polymyositis; psoriasis; Reiter's syndrome; rheumatoid arthritis; scleroderma; Sjogren's syndrome; systemic anaphylaxis; systemic lupus erythematosus; systemic sclerosis; thrombocytopenic purpura; ulcerative colitis; uveitis; Werner syndrome; and viral, bacterial, fungal, parasitic, protozoal, and helminthic infections.

Data regarding ubiquitination in apoptotic cells and in pathologies associated with the misregulation of apoptosis also can be obtained using methods according to the invention.

In a further embodiment, data regarding ubiquitination in cardiac cells and cells from patients exhibiting a cardiac disease or at risk for a cardiac disease are obtained. In one aspect, the disease is an infarction or a condition relating to ischemia. In another aspect, the disease is cardiomyopathy.

Another aspect of the invention provides for kits for detecting and/or quantifying a polypeptide modification, such as ubiquitination. In one embodiment, the kit comprises a ubiquitin remnant specific binding partner and one or more components, including, but not limited to: a protease, preferably trypsin; a ubiquitinated molecule comprising known ubiquitination sites; acetonitrile; silica resin; heptafluorobutyric acid; urea (e.g., 8M urea); a sample plate for use with a mass spectrometer; a light-absorbent matrix; an ion exchange resin; software for analyzing mass spectra (e.g., such as SEQUEST); fused silica capillary tubing; and access to a computer memory comprising data files storing information relating to ubiquitination sites for a plurality of polypeptides for a plurality of different cells. Access may be in the form of a computer readable program product comprising the memory, or in the form of a URL and/or password for accessing an internet site for connecting a user to such a memory.

EXAMPLES

Example 1

Both polyclonal and monoclonal antibodies capable of recognizing the remnant of ubiquitin left from ubiquitinated proteins after digestion with the protease trypsin were generated. These antibodies were generated using a synthetic peptide library immunogen with the sequence CXXXXXXK (GG)XXXXXX, i.e., a Cysteine residue at the peptide amino-terminus, 6 "X" residues (X=any amino acid selected from all common amino acids excluding cysteine and tryptophan), a lysine residue ("K") that has been modified by addition of a Glycine-Glycine dipeptide to the epsilon-amino group of that lysine residue and 6 more "X" residues.

Polyclonal antibodies were generated by injecting rabbits with the peptide library immunogen described above conjugated either to keyhole limpet hemocyanin (KLH) or blue carrier protein. K(GG)-specific polyclonal antibodies from 6 rabbits: BL3415, BL3416, BL4933, BL4934, BL4935, BL4936.

BL4933, BL4935 were used as starting material for monoclonal antibody development.

A monoclonal antibody from BL4933 was cloned and named recombinant antibody #3925 (D4A7A10). An additional monoclonal antibody was cloned from BL4935 (D24B6G9).

Table 1 Shows the Different Monoclonal and Polyclonal Anti-Ubiquitin Remnant Antibodies of the Invention.

| Monoclonal anti-Ubiquitin Remnant Antibodies | Polyclonal anti-Ubiquitin Remnant Antibodies |
|---|---|
| | BL3415 |
| | BL3416 |
| D4A7A10 | BL4933 |
| | BL4934 |
| D28B6G9 | BL4935 |
| | BL4936 |

The heavy chain amino acid sequence of the D4A7A10 clone is provided in SEQ ID NO: 1. The light chain amino acid sequence of the D4A7A10 clone is provided in SEQ ID NO: 2. For the D4A7A10 clone (i.e., antibody #3925), using the CDR-defining rules set forth above, the CDR regions for the heavy and light chain are as follows:

```
Heavy Chain:
CDR1
                                    (SEQ ID NO: 3)
GFTISSNYYIYWV

CDR2
                                    (SEQ ID NO: 4)
CIYGGSSGTTLYASWAKG

CDR3
                                    (SEQ ID NO: 5)
DFRGADYSSYDRIWDTRLDL

Light Chain:
CDR1
                                    (SEQ ID NO: 6)
QSSENVYNKNWLS

CDR2
                                   (SEQ ID NOL: 7)
KASTLAS

CDR3
                                    (SEQ ID NO: 8)
AGDYGGTGDAFV
```

The skilled artisan can readily determine the CDRs for the other antibodies disclosed herein including, without limitation, the antibody D24B6G9 cloned from BL4935.

Example 2

Characterization and Screening of Ubiquitin Tag Motif Antibodies. Anti-ubiquitin remnant peptide antibodies were characterized by differential peptide ELISA against antigen peptides CXXXXXXK(GG)XXXXXX (C02-1257) and control peptides CXXXXXXKXXXXXX (173-92A). All antibodies gave strong positive signals with antigen peptides and showed no binding with control peptides. Antibodies were validated by the peptide immunoprecipitation-MS methods described below by identifying ubiquitin-modified peptides in a trypsin-digested Jurkat cell lysate: antibodies passed this validation test when their use resulted in identification of most of the seven known ubiquitination sites in ubiquitin itself. These seven sites are shown in Table 2. Note that the some of the sites are represented in more than one peptide produced by trypsin digestion due to more than one trypsin cleavage sequence near the ubiquitinated site and/or due to more than one ubiquitinatable lysine residue in the peptide. For example, the ubiquitinated site at residue 48 is found in three tryptic peptides (see Table 2).

TABLE 2

Known Ubiquitination Sites in Ubiquitin (where the asterisk following the lysing residue (i.e, K*) indicates the ubiquitinated residue)

| Residue Number | Peptide Sequences |
|---|---|
| 6 | MQIFVK*TLTGK (SEQ ID NO: 9) |
| 11 | TLTGK*TITLEVEPSDTIENVK (SEQ ID NO: 10) |
| | TLTGK*TITLEVEPSDTIENVKAK (SEQ ID NO: 11) |
| 27 | TITLEVEPSDTIENVK*AKIQDKEGIPPDQQR (SEQ ID NO: 12) |
| 29 | AK*IQDKEGIPPDQQR (SEQ ID NO: 13) |
| | AK*IQDK*EGIPPDQQR (SEQ ID NO: 14) |
| 33 | IQDK*EGIPPDQQR (SEQ ID NO: 15) |
| | AKIQDK*EGIPPDQQR (SEQ ID NO: 16) |
| | AK*IQDK*EGIPPDQQR (SEQ ID NO: 17) |
| 48 | LIFAGK*QLEDGR (SEQ ID NO: 18) |
| | LIFAGK*QLEDGRTLSDYNIQK (SEQ ID NO: 19) |
| | LIFAGK*QLEDGRTLSDYNIQKESTLHLVLR (SEQ ID NO: 20) |
| 63 | TLSDYNIQK*ESTLHLVLR (SEQ ID NO: 21) |

The antibodies of the invention were designed to recognize any peptide that contains ubiquitinated lysine residues regardless of surrounding peptide sequences. To illustrate the general context-independent recognition properties of one of these antibodies, the heat map shown in FIG. 2 shows the frequency of amino acids found with the BL4936 polyclonal antibody in a study of four mouse tissues. The studies were similar to the study described below in Example 3. Briefly, and by way of example, the cellular proteins are isolated from the tissue and digested with trypsin protease. Peptide purification was carried out, e.g., using Sep-PakC18 columns as described in Rush et al., U.S. Pat. No. 7,300,753). Following purification, peptides are lyophilized and then resuspended in MOPS buffer (50 mM MOPS/NaOH pH 7.2, 10 mM Na2HPO4, 50 mM NaCl) and insoluble material removed by centrifugation at 12,000×g for 10 minutes. The anti-ubiquitin remnant antibodies of the invention were coupled non-covalently to protein G agarose beads (Roche) at 4 mg/ml beads overnight at 4° C. After coupling, antibody-resin was washed twice with PBS and three times with MOPS buffer. Immobilized antibody (40 ul, 160 ug) was added as a 1:1 slurry in MOPS IP buffer to the solubilized peptide fraction, and the mixture was incubated overnight at 4° C. The immobilized antibody beads were washed three times with MOPS buffer and twice with ddH20. Peptides were eluted twice from beads by incubation with 50 IA of 0.15% TFA for 15 minutes each, and the fractions were combined and analyzed by LC-MS/MS mass spectrometry.

Altogether 1458 non-redundant peptides were included in the frequency map shown in FIG. 2. The map clearly shows there are no strongly preferred amino acids at least seven residues to the amino-terminal side of K(GG) modification sites (−7 to −1 in FIG. 2) or at least seven residues to the carboxyl-terminal side of K(GG) modification sites (1 to 7 in FIG. 2).

What is claimed is:

1. A method of isolating peptides comprising lysine residues having a ubiquitin remnant comprising:
   (a) digesting a sample of proteins with a hydrolyzing agent to produce a mixture of cleavage peptides;
   (b) contacting the mixture of cleavage peptides with an antibody or a specific binding fragment thereof that specifically binds a ubiquitin remnant, wherein the antibody or specific binding fragment thereof comprising a heavy chain CDR1 as set forth in SEQ ID NO:3, a heavy chain CDR2 as set forth in SEQ ID NO:4, a heavy chain CDR3 as set forth in SEQ ID NO:5, a light chain CDR1 as set forth in SEQ ID NO:6, a light chain CDR2 as set forth in SEQ ID NO: 7, and a light chain CDR3 as set forth in SEQ ID NO:8;
   (c) eluting cleavage peptides that have specifically bound to the antibody or specific binding fragment thereof; and
   (d) purifying the cleavage peptides, such that peptides comprising lysine residues having a ubiquitin remnant are detected.

2. The method of claim 1, wherein the proteins are a suspension of cells, a subcellular fraction of a cell line or tissue, or a cellular lysate.

3. The method of claim 1, wherein the hydrolyzing agent is a protease.

4. The method of claim 3, wherein the protease is trypsin.

5. The method of claim 1, wherein the antibody or specific binding fragment thereof is linked to a bead, polystyrene matrix, protein G agarose beads, agarose gel matrix, or nitrocellulose membrane.

6. The method of claim 1, wherein the antibody or specific binding fragment thereof is linked to an agarose bead.

7. The method of claim 1, wherein the cleavage peptides are purified by HPLC or reversed phase liquid chromatography.

8. The method of claim 1, wherein after the cleavage peptides are purified they are subjected to liquid chromatography MS/MS analysis.

* * * * *